United States Patent
Strader et al.

(10) Patent No.: US 11,004,552 B2
(45) Date of Patent: May 11, 2021

(54) METHOD AND APPARATUS FOR COMPLETING PRESCRIPTION FOR ALLERGEN COCKTAIL WITH PATCH

(71) Applicant: ROCA MEDICAL LTD., London (GB)

(72) Inventors: James Strader, Austin, TX (US); Jovan Hutton Pulitzer, Frisco, TX (US)

(73) Assignee: ROCA MEDICAL LTD., London (GB)

( * ) Notice: Subject to any disclaimer, the term of this patent is extended or adjusted under 35 U.S.C. 154(b) by 423 days.

(21) Appl. No.: 15/621,798

(22) Filed: Jun. 13, 2017

(65) Prior Publication Data

US 2017/0340576 A1    Nov. 30, 2017

Related U.S. Application Data

(63) Continuation-in-part of application No. 15/235,067, filed on Aug. 11, 2016, now Pat. No. 10,872,313, which is a continuation-in-part of application No. 15/171,920, filed on Jun. 2, 2016.

(60) Provisional application No. 62/349,626, filed on Jun. 13, 2016, provisional application No. 62/203,819, filed on Aug. 11, 2015, provisional application No. 62/169,787, filed on Jun. 2, 2015, provisional application No. 62/169,785, filed on Jun. 2, 2015.

(51) Int. Cl.
```
G16H 20/10      (2018.01)
A61K 9/70       (2006.01)
G06Q 30/06      (2012.01)
G06Q 10/10      (2012.01)
G16H 70/40      (2018.01)
G16H 40/20      (2018.01)
```

(52) U.S. Cl.
CPC ........... *G16H 20/10* (2018.01); *A61K 9/7046* (2013.01); *G06Q 10/10* (2013.01); *G06Q 30/0635* (2013.01); *G16H 40/20* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 4,666,441 A * | 5/1987 | Andriola | A61K 9/7084 424/448 |
| 6,488,937 B1 | 12/2002 | Smits | |
| 2003/0082212 A1 | 5/2003 | Smits | |
| 2004/0185055 A1 * | 9/2004 | Glenn | A61K 9/7061 424/184.1 |
| 2006/0020514 A1 | 1/2006 | Yered | |
| 2006/0212318 A1 | 9/2006 | Dooley et al. | |
| 2009/0169602 A1 | 7/2009 | Senti et al. | |

OTHER PUBLICATIONS

PCT: European Patent Office Searching Authority, International Search Report and Written Opinion of PCT/IB2015/001330 (related application), dated Oct. 5, 2015, 14 pgs. Oct. 5, 2015.
Baumann L.S. et al., "Lip Silicone Granulomatous Foreign Body Reaction Treaded with Aldara (Imiquimod 5%)", Dermatologic Surgery Apr. 1, 2003 US, vol. 29, No. 4, Apr. 1, 2003 (Apr. 1, 2003), pp. 429-432, XP002745005, ISSN: 1076-0512, p. 429, left-hand col., paragraph middle. Apr. 1, 2003.
Prieto-Garcia Alicia et al: "Autoimmune Progesterone Dermatitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, p. 1121.e9, left-hand col. p. 1121.e12, left-hand col., paragraph top Mar. 1, 2001.
Cox et al., J. Allergy Clin. Immunol. 2011; 127(1 ):S1-S55 Jan. 1, 2011.
El Maghraby et al. Eur. J. Pharma. Sci. 2008; 34:203-222 Apr. 18, 2008.
PCT: European Patent Office Searching Authority, International Search Report and Written Opinion of PCT/IB2016/001332 (related application), dated Nov. 24, 2016, 13 pgs. Nov. 24, 2016.
E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

* cited by examiner

*Primary Examiner* — Robert A Wax
*Assistant Examiner* — Randeep Singh

(57) ABSTRACT

A method for creating a multi-antigen patch, comprising providing one or more transdermal patch sheets having a plurality of single dose transdermal patches residing thereon, wherein each one of the plurality of single dose transdermal patches includes an antigen at a particular dilution level disposed within a carrier, removing one or more of the plurality of single dose transdermal patches from the one or more transdermal patch sheets, adhering the one or more of the plurality of single dose transdermal patches to a backing, wherein the backing allows for multiple single dose transdermal patches to be adjacently adhered thereon, and covering the plurality of transdermal patches adhered to the backing with a peelable release liner.

5 Claims, 25 Drawing Sheets

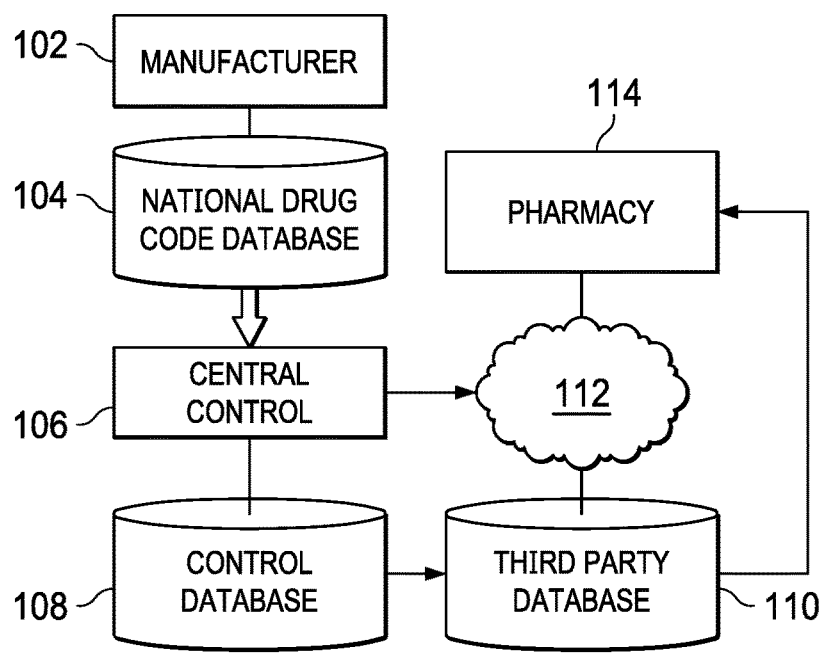
FIG. 1
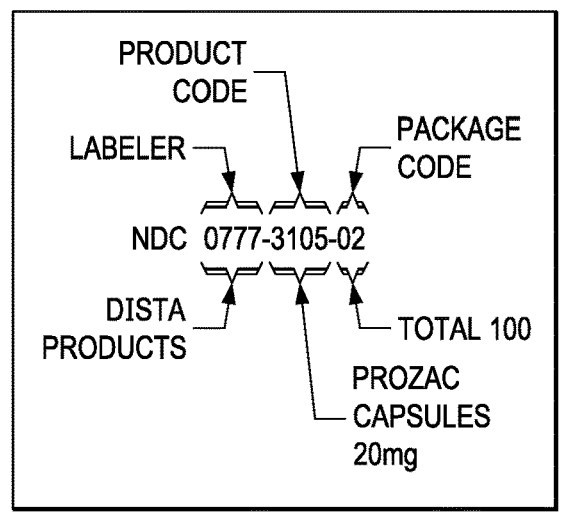
FIG. 1A
THIRD PARTY DATABASE
| NATIONAL DRUG CODE | AVERAGE WHOLESALE PRICE | INFORMATION | |
|---|---|---|---|
| XX.XX | $4.44 | AAA | |
| YY.YY | $5.44 | BBB | |
| ZZ.ZZ | $6.44 | CCC | |
| | | | |
FIG. 2

```
                    ┌─────────┐
         1102 ──────│  START  │
                    └─────────┘
                         │
                         ▼
              ┌──────────────────────────┐
         1104─│ Rx CONCENTRATE FROM VENDOR│
              └──────────────────────────┘
                         │
                         ▼
              ┌──────────────────────────┐
              │   TRANSFER DESIRED AMOUNT │
         1108─│    TO INTERMEDIATE BOTTLE │
              │    WITH BUFFERED SALINE   │
              └──────────────────────────┘
                         │
                      1110
                      ◇ LAST DILUTION? ◇
                  YES /        \ NO
              1116 (END)         ▼
                           EXTRACT 1mL FROM CURRENT  ─ 1112
                                  │
                                 INC  ─ 1114
```

FIG. 11

```
  ┌─────────────────────────────────┐    ┌──────────────┐
  │ LIQUID ANTIGEN OR COMBINATION   │    │ FINAL CARRIER│
1202│ OF ANTIGENS SUSPENDED IN       │    │    1210      │
  │ STERILE AGENT (FROM VENDOR)     │    └──────────────┘
  └─────────────────────────────────┘
              │
  1204 ── ANTIGEN DILUTION
              │
  1206 ──────── COMBINATION ────────
              │
  1212 ── COMBINED ANTIGEN (DILUTED)/ENCAPSULATION STORAGE
```

FIG. 12

| SINGLE ANTIGEN TABLE | | | | | | | | |
|---|---|---|---|---|---|---|---|---|
| NDC | ANTIGEN | DILUTION PROCEDURE | D1 (BASE) | D2 | D3 | D4 | D5 | D6 |
| XXX | CAT | STANDARD | X1 | X2 | X3 | X4 | X5 | X6 |
| | | | Y1 | Y2 | Y3 | Y4 | Y5 | Y6 |
| | | | Z1 | Z2 | Z3 | Z4 | Z5 | Z6 |
| ooo | ooo | ooo | ooo | ooo | ooo | ooo | ooo | ooo |
| YYY | DOG | STANDARD | X1 | X2 | X3 | X4 | X5 | X6 |
| | | | Y1 | Y2 | Y3 | Y4 | Y5 | Y6 |
| | | | Z1 | Z2 | Z3 | Z4 | Z5 | Z6 |
| ooo | ooo | ooo | ooo | ooo | ooo | ooo | ooo | ooo |

FIG. 16

| DILUTION PROCEDURE | D1 | D2 | D3 | D4 | D5 | D6 |
|---|---|---|---|---|---|---|
| S1 | Z1 | Z2 | Z3 | Z4 | Z5 | Z6 |
| S2 | Z1' | Z2' | Z3' | Z4' | Z5' | Z6' |
| S3 | Z1" | Z2" | Z3" | Z4" | Z5" | Z6" |

FIG. 16A

| NDC BASE | ANTIGEN | DILUTION PROCEDURE | D1 | D2 | D3 | D4 | D5 | D6 |
|---|---|---|---|---|---|---|---|---|
| XXX (1702) | $A_{n-2}$ | STANDARD | $X_1$ | $X_1$ | $X_1$ | $X_1$ | $X_1$ | $X_1$ |
|  | $A_{n-1}$ |  | $X_1$ | $X_1$ | $X_1$ | $X_1$ | $X_1$ | $X_1$ |
|  | $A_n$ |  | $X_1$ | $X_1$ | $X_1$ | $X_1$ | $X_1$ | $X_1$ |
| ○○○ | ○○○ | ○○○ | ○○○ | ○○○ | ○○○ | ○○○ | ○○○ | ○○○ |

METHOD AND APPARATUS FOR COMPLETING PRESCRIPTION FOR ALLERGEN COCKTAIL WITH PATCH

CROSS-REFERENCE TO RELATED APPLICATIONS

This application is a Continuation-in-Part application of U.S. patent application Ser. No. 15/235,067, filed Aug. 11, 2016, entitled METHOD FOR REPURPOSING NDC CODES IN A PHARMACEUTICAL DATABASE FOR VENOM DERIVED ALLERGENS INVOLVED IN VENOM IMMUNOTHERAPY. U.S. application Ser. No. 15/235,067 is a Continuation-in-Part application of U.S. patent application Ser. No. 15/171,920, filed Jun. 2, 2016, entitled METHOD FOR MANAGING REIMBURSEMENTS FOR PREVIOUSLY NON DATABASE ALLERGENS, which claims the benefit of U.S. Provisional Application No. 62/169,787, filed on Jun. 2, 2015, entitled METHOD FOR REPURPOSING NDC CODES IN A PHARMACEUTICAL DATABASE FOR ALLERGENS, and to U.S. Provisional Application No. 62/169,785, filed on Jun. 2, 2015, entitled METHOD FOR MANAGING REIMBURSEMENTS FOR PREVIOUSLY NON DATABASE ALLERGENS. U.S. application Ser. No. 15/235,067 also claims the benefit of U.S. Provisional Application No. 62/203,819, filed on Aug. 11, 2015, and entitled METHOD FOR REPURPOSING NDC CODES IN A PHARMACEUTICAL DATABASE FOR VENOM DERIVED ALLERGENS INVOLVED IN VENOM IMMUNOTHERAPY, and to U.S. Provisional Application No. 62/349,626, filed on Jun. 13, 2016, entitled METHOD AND APPARATUS FOR COMPLETING PRESCRIPTION FOR ALLERGEN COCKTAIL WITH PATCH. This application also claims the benefit of and/or priority to U.S. Provisional Application No. 62/349,626, filed Jun. 13, 2016, entitled METHOD AND APPARATUS FOR COMPLETING PRESCRIPTION FOR ALLERGEN COCKTAIL WITH PATCH. U.S. patent application Ser. Nos. 15/235,067, 15/171,920, 62/169,787, 62/169,785, 62/203,819, and 62/349,626 are herein incorporated by reference in their entirety.

TECHNICAL FIELD

The following disclosure relates to repurposing an existing database related to the pharmaceutical industry and reimbursement for such things as allergens that are not currently supported in the database.

BACKGROUND

Currently, allergens are not readily reimbursed when received from a pharmacist for the simple reason that the National Drug Code (NDC) code is not included in the database to which the pharmacist has access. Without an NDC code in the database, the pharmacist cannot access that information. By not being able to access information, the pharmacist cannot interface with a benefits provider for reimbursements nor can they have access to the Average Wholesale Price (AWP), which is the benchmark that has been used for many years for pricing and reimbursement of prescription drugs for both government and private payers. Initially, this AWP was intended to represent the average price that wholesalers used to sell medications to providers, such as physicians, pharmacies, and other customers. However, the AWP is not a true representation of actual market prices for either generic or brand drug products. AWP has often been compared to the "list price" or "sticker price," meaning it is an elevated drug price that is rarely what is actually paid. AWP is not a government-regulated figure, does not include buyer volume discounts or rebates often involved in prescription drug sales, and is subject to fraudulent manipulation by manufacturers or even wholesalers. As such, the AWP, while used throughout the industry, is a controversial pricing benchmark.

The AWP may be determined by several different methods. The drug manufacturer may report the AWP to the individual publisher of drug pricing data, such as Medi-Span. The AWP may also be calculated by the publisher based upon a mark-up specified by the manufacturer that is applied to the wholesale acquisition cost (WAC) or direct price (DIRP). The WAC is the manufacturer's list price of the drug when sold to the wholesaler, while the DIRP is the manufacturer's list price when sold to non-wholesalers. Typically a 20% mark-up is applied to the manufacturer-supplied WAC or DIRP, which results in the AWP figure.

The publishers then in turn sell these published AWPs to government, private insurance, and other buyers of prescription drugs, who use these data tables to determine reimbursement and retail prices. Because AWP is a component of the formulas used to determine reimbursement, elevated AWP numbers can drastically increase the dollar amount that government, private insurance programs, and consumers with coinsurance must pay.

Pharmacies typically buy drugs from a wholesaler and then sell them to the public. Many patients have coinsurance or copayments, where they only pay for a portion of their prescription cost. The insurance company then pays the rest of the cost (the reimbursement) to the pharmacy. Insurance companies include prescription benefit manager (PBM), health maintenance organization (HMO) or government programs, such as Medicaid or Medicare Part B or D. In addition, the pharmacy receives a dispensing fee for filling the prescription. Fees are, for example, set between $3 to $5 per prescription, but may vary by state.

Reimbursements are based on AWPs. However, pharmacies purchase drugs based on the WAC. The difference between the WAC (what the pharmacy actually paid for the drug) and the reimbursement from insurance (based on AWP) is known as the spread, and equates to the profit that the pharmacy receives.

Market pricing on brand drugs tend to be about 16.6 percent less than the AWP. However, the relation of AWP to generic pricing is not clear. Older generics tend to have a large spread between the AWP and WAC, which in turn gives a large spread, and higher profit margins for the pharmacy or other provider of the drug. Many payers, such as PBMS or HMOs, will determine a maximum allowable cost (MAC) pricing on generics to avoid being overcharged. Newer generic products, compared to older generics, may not have as favorable of a spread, thus the need for MAC.

Collusion between AWP publishers and wholesalers to artificially inflate the AWP, and in turn increase the spread, has led to court cases in the U.S. In these cases, it was alleged that increasing the spread benefited the wholesaler because customers (pharmacies and large institutions) were more likely to buy from them than a competing wholesaler where the spread was not as desirable. The publisher of AWPs profited because pharmacies were more likely to buy the pricing lists from the publisher that noted the higher AWPs used in calculating the spread, than to buy them from other publishers with lower AWPs. Due to this pricing fraud, many payers, including government payers, are no longer using AWP for pricing, and are switching to other more transparent pricing benchmarks, such as WAC or AMP (average manufacturers price). However, AWP may still be found in use in the U.S. because it has been the standard for decades.

However, in order for a pharmacist to access the AWP and to be able to interface with benefits providers, the product associated with an NDC must be in the database. Currently, allergens are on item that does not exist in the database.

SUMMARY

In one embodiment, the present disclosure provides a method for creating a multi-antigen patch. The method includes providing one or more transdermal patch sheets having a plurality of single dose transdermal patches residing thereon, wherein each one of the plurality of single dose transdermal patches includes an antigen at a particular dilution level disposed within a carrier, removing one or more of the plurality of single dose transdermal patches from the one or more transdermal patch sheets, adhering the one or more of the plurality of single dose transdermal patches to a backing, wherein the backing allows for multiple single dose transdermal patches to be adjacently adhered thereon, and covering the plurality of transdermal patches adhered to the backing with a peelable release liner.

BRIEF DESCRIPTION OF THE DRAWINGS

For a more complete understanding, reference is now made to the following description taken in conjunction with the accompanying Drawings in which:

FIG. 1 illustrates a general diagrammatic view of the overall interface of basic databases;

FIG. 1A illustrates an NDA code;

FIG. 2 illustrates a diagrammatic view of a database that is populated by a central control system;

FIG. 11 illustrates a process flow for diluting an antigen extract;

FIG. 12 illustrates a process flow for the overall distribution chain;

FIG. 16 illustrates a diagrammatic view of a table in a relational database relating distributed doses back to NDC-bearing dose;

FIG. 16A illustrates a diagrammatic view of a table showing the dilution procedure;

DETAILED DESCRIPTION

Figure 3:
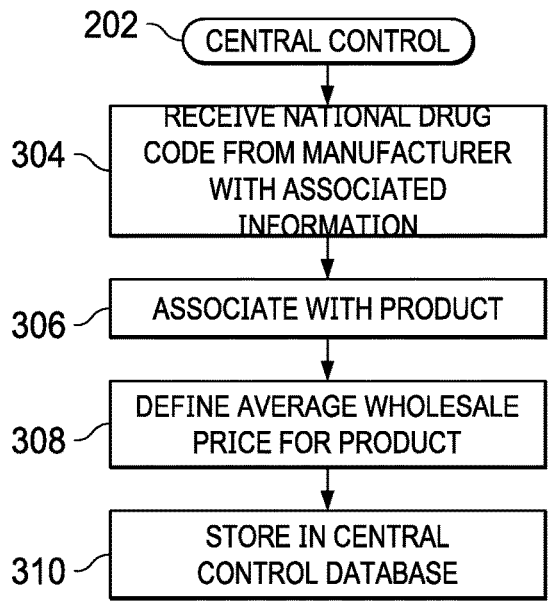
FIG. 3 illustrates a flow chart for the operation at the central control system for receiving NDCs from the manufacturer.

Referring now to FIG. 1, there is illustrated a diagrammatic view of the overall system for transferring NDCs between systems. The NDC, or National Drug Code, is a unique 10-digit, 3-segment number. It is a universal product identifier for human drugs in the United States. The code is present on all nonprescription (OTC) and prescription medication packages and inserts in the U.S. The 3 segments of the NDC identify the labeler, the product, and the commercial package size. The first set of numbers in the NDC identifies the labeler (manufacturer, repackager, or distributer). The second set of numbers is the product code, which identifies the specific strength, dosage form (i.e, capsule, tablet, liquid) and formulation of a drug for a specific manufacturer. Finally, the third set is the package code, which identifies package sizes and types. The labeler code is assigned by the FDA, while the product and package code are assigned by the labeler.

For example, the NDC for a 100-count bottle of Prozac 20 mg is 0777-3105-02. The first segment of numbers identifies the labeler. In this case, the labeler code "0777" is for Dista Products Company, the labeler of Prozac. The second segment, the product code, identifies the specific strength, dosage form (i.e, capsule, tablet, liquid) and formulation of a drug for a specific manufacturer. In our case, "3105" identifies that this dosage form is a capsule. The third segment is the package code, and it identifies package sizes and types. Our example shows that the package code "02" for this bottle of Prozac identifies that 100 capsules are in the bottle. The FDA maintains a searchable database of all NDC codes on their website. This is illustrated in FIG. 1A.

The NDC codes are unique codes that are applied for and assigned to specific individuals to be associated with specific products. Each manufacturer of allergens, for example, has a unique NDC associated with the allergen that they provide, which is assigned to that manufacture for that allergen based upon their applying for such. The manufacturer, therefore, has full ownership of that NDC. In order for that NDC to appear in a database with the associated information the approval of that manufacture is required. For example, manufacturer of a well-known drug will provide information to the database and populate that database and the record associated with that NDC with the information regarding that allergen associated with that NDC but they will also define what the AWP is for that allergen. It is the manufacturer, not the person that controls the NDC of the manufacturer, that controls what is in database, including the AWP. Additionally, it should be noted that a distributor could actually apply for an NDC and could populate or associate with that NDC information regarding a particular allergen. They could actually place this NDC that they own, this being a unique NDC, in a database with another NDC, a different and unique NDC, that will be associated with basically the same allergen. This, of course, would provide some NDC contention within the database which is to be avoided if possible. In addition, if a manufacturer were to expand their offerings such that bulk allergens were packaged in different bottles at different dosages, this would require an NDC code for that particular configuration. This, again, would be NDC codes that were owned by manufacturer and uniquely identify the particular allergen and the configuration and dosage of that allergen. Currently, allergens are distributed in bulk quantities.

Thus, a manufacturer 102 has associated therewith its own proprietary database 104 to store their NDCs in association with information for that particular NDC. This can be provided to a central control center 106. The central control center 106 desires to have exclusive access to these NDCs of the manufacturer 102. This is the primary reason that these NDCs do not exist in any other database. Typically, the central control center 106 would have some type of contractual relationship with the manufacturer 102 for the purpose of maintaining some type of exclusivity with respect to the manufacturer's NDCs. Thereafter, these NDCs are stored in a central control database 108 at the central control center 106, in this database 108, the central control center 106 can modify and augment the information. Primarily, the main aspect that they add is the AWP, but they can reformat and reorganize the informative part of database associated with the particular allergen. This allows the central control 102 to thus control this AWP associated with each NDC of a particular manufacturer. There is, of course, the wholesale cost charged for the allergen to an end user such as a pharmacist, but the AWP is the benchmark price, again noting that the AWP is assigned to the NDC by recent control center 106 and not by the manufacture. This is not necessarily the price that the pharmacist, for example, will charge to the customer but, rather, it is the benchmark price. Further, this is not even the price that will be reimbursed to the pharmacist even if the pharmacist billed the customer for such. Thus, of course, this would not result in any type of price-fixing; rather, all that is controlled by the central control center 106 is the inclusion of AWP within the database. This AWP can be utilized by the reimbursing entities and the such for centering on a final reimbursement price.

With respect to the third-party database 110, this database is a database that can be accessed by both the pharmacist and the reimbursing entity such as the insurance companies. The pharmacist accesses this database 110 for the purpose of determining if the NDC for the particular prescribed allergen exists within the database. If so, then the pharmacist can access not only information about the allergen but also the AWP for that allergen. A claim can then be put in for the allergen with that NDC to, for example, the patient's insurer. The patient's insurer, when receiving a claim, can access the database 110 to determine if this is in fact an NDC that exists in the database and has an AWP associated therewith. By having the AWP associated with the NDC, this allows the overall claim to be adjudicated.

The data associated with these allergens is then downloaded into a third party database 110 associated with a third-party information provider. This information provider is one of many information providers that provide access through a network 112 to a pharmacy 114. It is noted, however, that the central control 106 first confirms that none of the NDCs associated with any of the allergens is actually currently in the third party database 110. Once these NDCs and their associated information and associated AWPs are stored in the third party database 110 by the simple control center 106, the central control center 106 has some control over both the information and the AWP associated with each of the NDCs. Thus, when a pharmacist receives a request from a physician to fill a prescription for an allergen for delivery to the physician, the pharmacist can access the third party database 110 and determined that this is, in fact, in the database and is a reimbursable prescription. It is not the fact that the information merely exists in a database but, rather, that an AWP is associated therewith that allows the claim made by the pharmacist to be adjudicated.

Referring now to FIG. 2, there is illustrated a diagrammatic view of the third party database 110 and a portion thereof populated by the central control center 106. This includes, in one column, NDCs for the various allergens, and a second column associated AWPs and in a third column information regarding the allergen associated with each of the NDCs. In a fourth column there would be provided information regarding the source of the allergen associated with that NDC, that being the provider of the particular allergen. In the present disclosed embodiment, there is an exclusive arrangement between the central control center 106 and the manufacture such that no other distributor or entity is allowed to populate a third-party database with that NDC and with another AWP. As such, and insurer, when viewing the third-party database 110, will only be presented with a single AWP for a given NDC. There will thus be no conflict between one provider and another provider.

Referring now to FIG. 3, there is illustrated a flowchart depicting the initial operation of populating the database 108. The central control center 106 initiates the process at a block 202 and proceeds to block 304 in order to receive the NDC from the manufacturer for a particular allergen with the associated information regarding the associated allergen. There is one associated with allergen in the database of the central control center 106 and also with allergens controlled by the central control center 106. The central control center 106 is typically associated with some type of distribution center such that, with respect to the information that they associate with the NDC in the database 108, the control center 106 and the entity associated there with are the distribution arm for that allergen, i.e., this is where the allergen is ordered from by the pharmacist. The program then proceeds to a block 308 wherein the AWP for that particular allergen and associated with that NDC is defined by the central control center 106. This is a number that is set at whatever level is determined to be correct and appropriate by the central control center 106. There are a number of reasons for the price being set at any level. There is, of course, some cost of buying an allergen from the manufacturer 102, the markup and expenses associated with the operation of the central control center 106, resulting in a wholesale price to the pharmacist. This wholesale price is not necessarily associated with the record that is stored in the database 110. However, it is this information that is utilized in determining what the AWP will be for that NDC and associated allergen. A number of factors, of course, enter into that calculation, including practical knowledge of how the insurance industry reimburses for allergens. After processing, the information is stored in the central control database 108.

Figure 4:
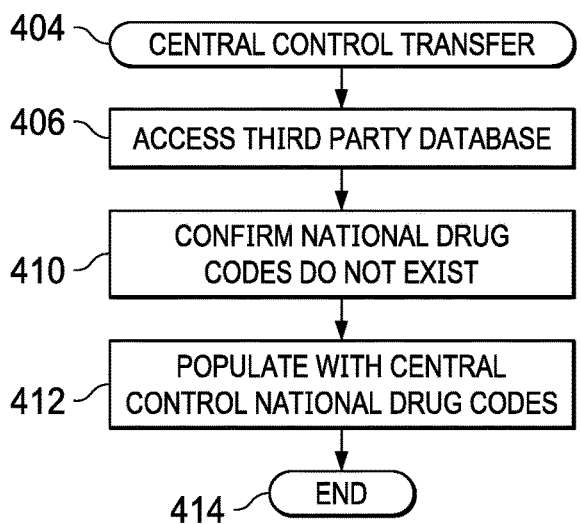
FIG. 4 illustrates a flow chart for the operation of populating third-party database by the central control system.

Referring now to FIG. 4, there is illustrated a flowchart depicting the transfer of data, which is initiated at a block 404 and then proceeds to a block 406 to access the third-party database 110 through the network 112. The program then flows to a function block 410 to confirm that no NDCs in the control database 108 exists within that third-party database 110 for the allergens that are desired to be populated within that third-party database 110, i.e., the manufacturer has not granted the right to another entity to populate that third-party database 110 nor have they done it without authorization. This will ensure that the central control center 106 has exclusive access for those particular NDCs associated with those particular allergens with respect to the third-party database 110. The program then flows to a function block 412 to populate the third-party database 110 with information from the control database 108, which, as described above, includes the information from the manufacturer, information regarding the central control center 106 as being a source of the allergen and the AWP for that allergen, all associated with the NDC assigned to the manufacturer for that allergen, this being a unique association between an NDC, information, the AWP and the provider of that AWP and allergen. The program that flows to a terminate block 414.

Once the third-party database 110 has been populated with the NDCs for the allergens from the central control center 106, this portion of the third-party database 110 will uniquely have all of the NDCs populated thereby directed to or pointed to or given a unique relationship with the central control center 106. The AWP is associated with each NDC but, this unique association of each NDC with the central control center 106 defines an ownership of that unique NDC by the central control center 106 and also uniquely defines the central control center 106 as the provider of the allergen(s) associated with that particular NDC or particular NDCs. By defining such a unique link, this allows the central control center 106 to be uniquely situated within the adjudication procedure or process with the insurer. Not only does the existence of the NDC for each of the allergens in the third-party database 110 provide the pharmacist with access to an AWP for that allergen the via the unique NDC and the insurer access to to such information also, but it also defines a unique link between all of those populated NDCs for the allergens to the central control center 106.

Figure 5:
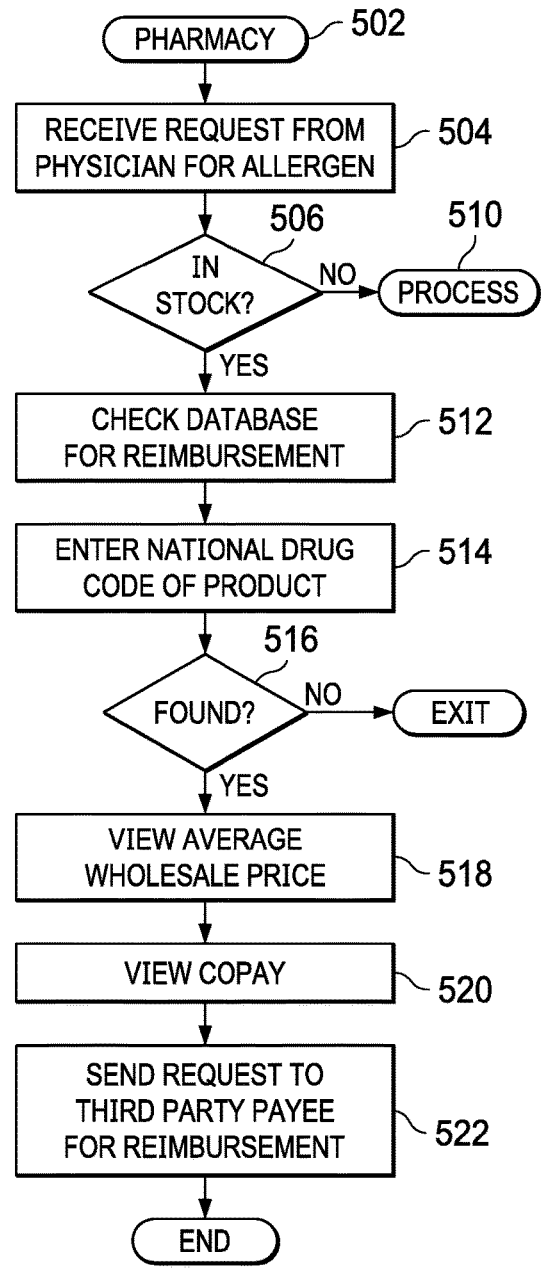
FIG. 5 illustrates a flow chart for the operation at the pharmaceutical location.

Referring now to FIG. 5, there is illustrated a flowchart for the operation at the pharmacy. This is initiated at a block 502 and then proceeds to a block 504 wherein the pharmacist receives a request from a physician for an allergen. This might actually be presented to the pharmacist by a patient which desires to receive the allergen for dilution and processing by the position or it may in fact be an already diluted allergen that could be actually self-administered by the patient. The program then flows to a decision block 506 to determine if the allergen is in stock. If the allergen is in stock, the program flows to a function block 512 to check the third-party database 110 for reimbursement and, if not, the program flows to a block 510 to process a stock item by whatever procedure the pharmacist utilizes. When checking the third-party database 110, the pharmacist enters the NDC code of the allergen, as indicated in a block 514. The program then flows to a decision block to determine if the NDC is found, this being block 516. If not found, the program exits and, if found, the program flows the function block 518 wherein the pharmacist can view the AWP for that allergen. This gives the pharmacist some idea as to what might be reimbursable in addition to the knowledge that this is in fact a reimbursable allergen, but also, the insurer itself can have access to third-party database 110 in order to provide information as to some type of potential co-pay. This just indicates the amount that the patient will pay at the counter. The pharmacist then can enter an amount that the pharmacist will claim that they want to be paid for this particular allergen, i.e., the claim that will be made to the insurer. It may be less than the AWP but not more than AWP. This, of course, is a function of what the pharmacist desires. This is indicated by block 520. Thus, there is provided a third-party database 110 heading information contained therein, which is controlled by the central control center 106 with respect to the allergens. Part of this is the AWP and part of it is the source for that allergen. The insurer has accents to this information and can utilize it to adjudicate a claim. Information from the insurer can be linked to this database indicating a co-pay, for example. With respect to this, and insurer can indicate that it will pay the entire cost of the particular allergen or indicate what percentage of the allergen that it will pay for. Sometimes, it is just a co-pay. However, for some very expensive allergens, the insurer may over time decide that it only pay a small percentage of the allergen. This will be on an allergen-by-allergen basis. By allowing this third-party database 110 to be controlled by the central control center 106 with respect to the cost for the particular allergen, this allows central control center 106 to control the adjudication of the particular allergen. The Program then flows to a function block to send a request to the third-party payee for reimbursement, as indicated by block 522.

The process for adjudicating any claim requires that some entity or party has worked with the insurance company or the reimbursing entity to negotiate the particular reimbursement or any benefits that are provided. If the pharmacist is apprised of an AWP in the database for a particular allergen, they at least have a price that they can charge for the product. For example, if the pharmacist has a product on the shelf with an NDC any position writes a prescription for that allergen, the pharmacist just needs to know how much to charge the patient. By accessing the third-party database 110, the AWP can be determined. However, that alone doesn't allow the pharmacist to determine whether benefits are associated with that particular allergen. In order to do that, there has to be some link between and an adjudicating party or entity. The pharmacist can select the NDC and a field (not shown) that directs the pharmacist to an adjudicating party or entity to provide information as to benefits that are available. If such indicates that benefits are available, then the armistice knows that they can make a claim to this adjudicating party.

In the current disclosed embodiment, the central control center 106 maintains the adjudicating database. The central control center 106 is responsible for interfacing with insurers and the such to provide these benefits. For example, if there are five major insurance companies that reimburse the pharmacist or even Medicare, the central control center 106 will make the arrangements for reimbursement and allow the pharmacist to determine whether the patient who may be associated with any of these reimbursement entities can receive benefits. If, for example, the patient had insurance with Insurer A, and central control center 106 had negotiated with Insurer A for certain benefits, this would be made available to the pharmacist. The benefits might provide for some type of co-pay which the pharmacist could charge to the patient and then the pharmacist could make a claim for the remaining value of the allergen to the adjudicating party, i.e., in this case the central control center 106. The central control center 106 would then process the claim and forward a check to the pharmacist. Since the central control center 106 populated the third-party database 110 with all of the NDCs, the central control center 106 has exclusive rights to adjudicate these NDCs and the associated allergens. Thus, this unique link from the third-party database 110 to the central control center 106 allows all claims to be adjudicated therethrough because the central control center 106 has exclusive control over these NDC for these allergens.

All of the NDCs, as noted hereinabove, or for allergens and allergens that are to be dispensed to a patient are a single dose allergen. Thus, each of the NDCs that would be obtained by the manufacturer would be for single dose allergens rather than bulk allergens that are currently provided.

Figure 6:
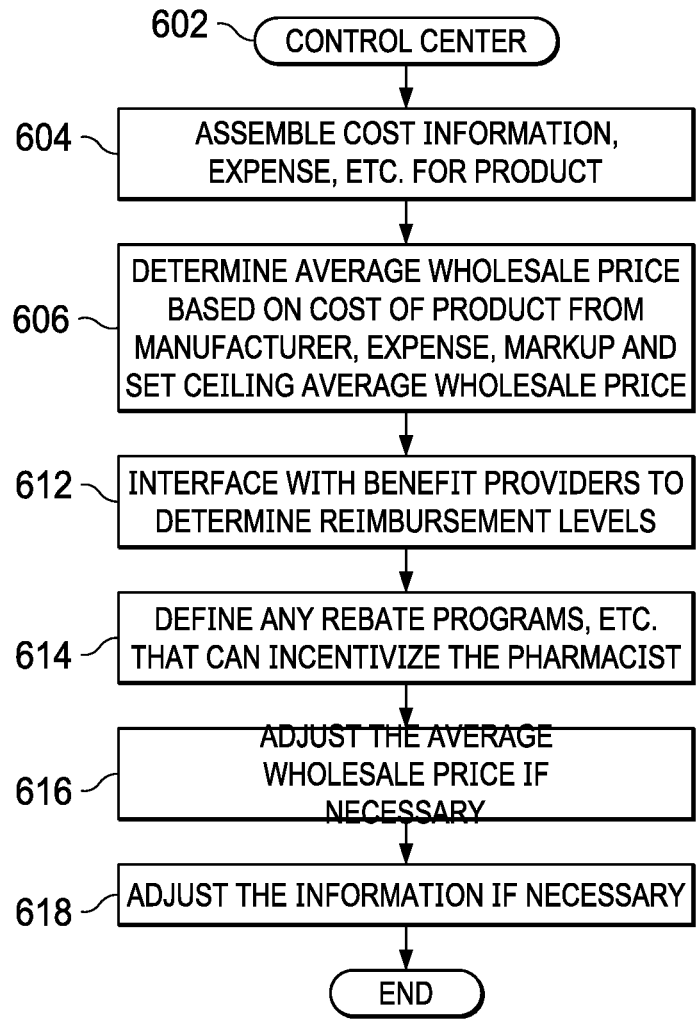
FIG. 6 illustrates a flow chart for the overall generation of the AWP and the interface with the benefit providers.

FIG. 6 illustrates a flow chart depicting the operation wherein the control center is able to determine the AWP by interfacing with the benefit providers. This is initiated at a block 602 and then proceeds to block 604 wherein the control center assembles the various cost information regarding the manufacturers cost to the control center, the expenses of storing the allergen at the control center, i.e., where the control center is the distributor and provider of the allergen, and what kind of markup or profit margin the control center expects to receive on an allergen. The program then flows a function block 606 to determine the AWP. This AWP is based on the information retrieved in block 604 and then a ceiling for the AWP is determined. This ceiling is a number that is arrived at by the control center based upon their knowledge of how the benefit providers reimburse pharmacists and the such. Since the AWP is a ceiling and the pharmacist cannot charge more than that, they provide a number that is a benchmark for the industry. By determining this benchmark, the insurance industry will typically center in on a lower reimbursable price, depending upon how valuable they think a particular allergen or the such is to the industry. For example, if they sold the product for $350 to the pharmacist, this being the wholesale price, they might set the AWP at $500. Over time, the pharmacist may actually make a claim for only $450 which, at first, the insurance copies may reimburse. After a time, the insurance industry may come to the conclusion that this allergen is only reimbursable at a rate of $400.

The program then flows to a function block 612 wherein a control center can interface with benefit providers to determine what the reimbursement levels are and, if necessary, adjust the AWP. However, they can also determine such things as rebate programs and incentives and the such that they can provide to the pharmacist, as indicated by a function block 614. Since they control the database they can also write information from the interface with that particular part of the database. Program then flows to a function block 616 to adjust the AWP if necessary and into a function block 618 to adjust the information in the database if necessary.

By way of a detailed look at, the overall operation of initially testing patient at the physician's office, writing a script for the patient and completing the prescription by processing that script at a pharmacist location or some type of compounding pharmacy operation. In general, it must be noted that each script is very patient-specific; that is, in a system that is unique to testing for allergens, it is necessary to determine which of multiple antigens must be combined in a desensitization program. It may be that, for example, a prick test initially indicates that the patient is highly allergic to cat fur, dog hair, various types of pollen and the such. After positive indication for these particular allergens, the physician can determine which antigens need to be combined in some type of prescribed dosage regimen. Since there are so many allergens that can exist and since each patient is an individual, this combination can be somewhat daunting if the desired the industry were to provide only that particular combination as a "drug" that has an NDC associated there with. This is practically impossible, of course.

Figure 7:
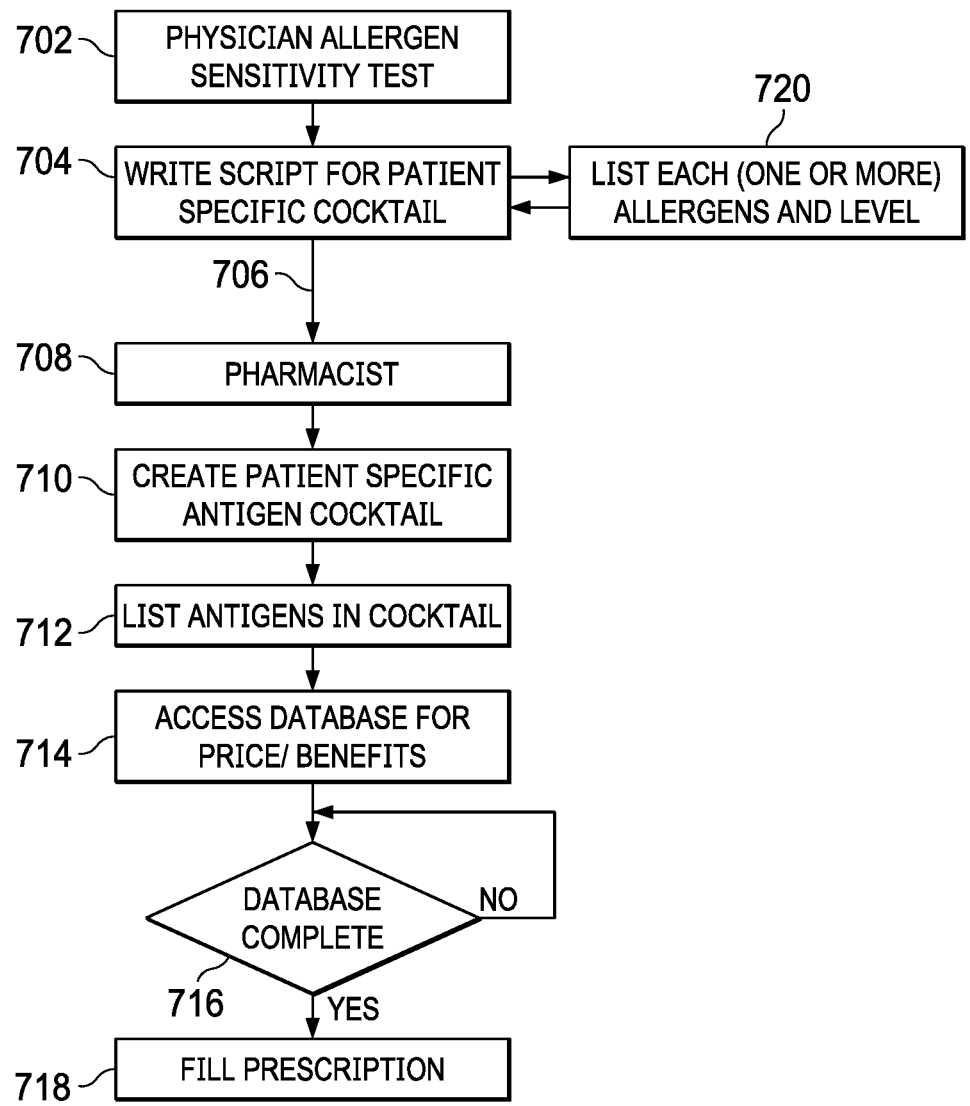
FIG. 7 illustrates a diagrammatic view of flow beginning at the prick test and following through to filling the prescription at the pharmacist location.

Referring now to FIG. 7, there is illustrated a flow diagram of the overall process of determining a particular combination of antigens to desensitize an individual and the regimen therefore. This is initiated at a block 702 wherein the physician subjects the patient to what is known as a "prick" test. This prick test is a test whereby the physician introduces a small amount of allergens into a small area on the skin of an individual. There can be multiple spots that are arranged in a grid on, for example, a portion of the back of the patient. These allergen locations are recorded and then they are observed over a certain period of time. There is also typically some type of base allergen that is provided such as a hypoallergenic antigen and a hyper allergenic antigen such that there is an area that will result in no response and as an area that will result in a guaranteed response. Upon observation, areas that elicit a positive response indicate that the patient is sensitive to that particular allergen. It may be that the patient is very sensitive to certain of the allergens and just mildly sensitive to others. The physician then determines which of the allergens need to be included in a desensitization program. For example, if an individual in Texas showed a positive response to some allergen that rarely occurred in Texas, the physician might not include that in a desensitization regimen.

Once the regimen is set upon for a particular patient, a script is then written by the physician, as indicated by block 704. This can be a script for a single antigen if that was all that was required for a desensitization program or it could be for a cocktail of multiple antigens. The physician will define the antigen or antigens that are to be included in the regimen, the dosage level and the carrier. For example, for the first desensitization level, the most diluted level of antigen will be utilized. Typically, the physician will require that the single antigen or cocktail of antigens be provided in a carrier such as saline or glycerol in a vial that will allow for a certain number of injections. It may be that the physician wants to prescribe for this first desensitization level a dosage that will allow for three injections per week for three weeks.

This script is then written and provided to the patient or it can be directly delivered to the pharmacist, as indicated by a path 706 to a block 708 indicating the pharmacist. The pharmacist then creates a patient-specific antigen cocktail, as indicated by block 710. The pharmacist then lists the antigens that are contained within the cocktail, noting that there could be a single antigen. This is indicated at a block 712 and then the pharmacist accesses the database for price and benefits. This is basically the Pharmacy Benefits Manager (PBM) database, which contains all of the drugs, etc., that are available for reimbursement. If the pharmacist, for example, looks up a particular antigen that was prescribed in the script and does not find it, this indicates that it is not something that can be reimbursed. If, however, this antigen exist within the database, it indicates both the AWP for that antigen and benefits associated therewith. All of this is pre-populated within the database. However, with respect specifically to any antigen, the NDC for that antigen will only be associated with the base concentrate level. The script, however, is for a particular diluted dosage of that particular antigen and even a combination of multiple antigens at that particular dosage. This database is accessed at a block 714 and then, after access is complete, as indicated by a decision block 716, the prescription is filled at a block 718. The operation of determining the particular AWP and benefits associated with any script for antigens at any dosage level, wherein the particular combination of antigens does not have particular NDC associated therewith nor does any antigen by itself have a particular NDC associated therewith, it is necessary to cross correlate this with an NDC that has an AWP associated therewith. Further, with respect to antigens specifically, the current NDC for any antigen is associated with the base concentrated material and this base concentrated material is too toxic to utilize at that concentration level. Thus, anything that is distributed to the patient will always be diluted from this base concentrated material. As will be described hereinbelow, it is always necessary to cross correlate any dosage level back to the NDC for the base concentrated material in order to determine benefits. Further, each of the scripts set forth by the physician will always have a list of each of the one or more allergens to which the patient exhibited a level of sensitivity thereto and the antigens associated there with. Further, the physician will determine the dosage level also. This is indicated by block 720.

Figure 8:
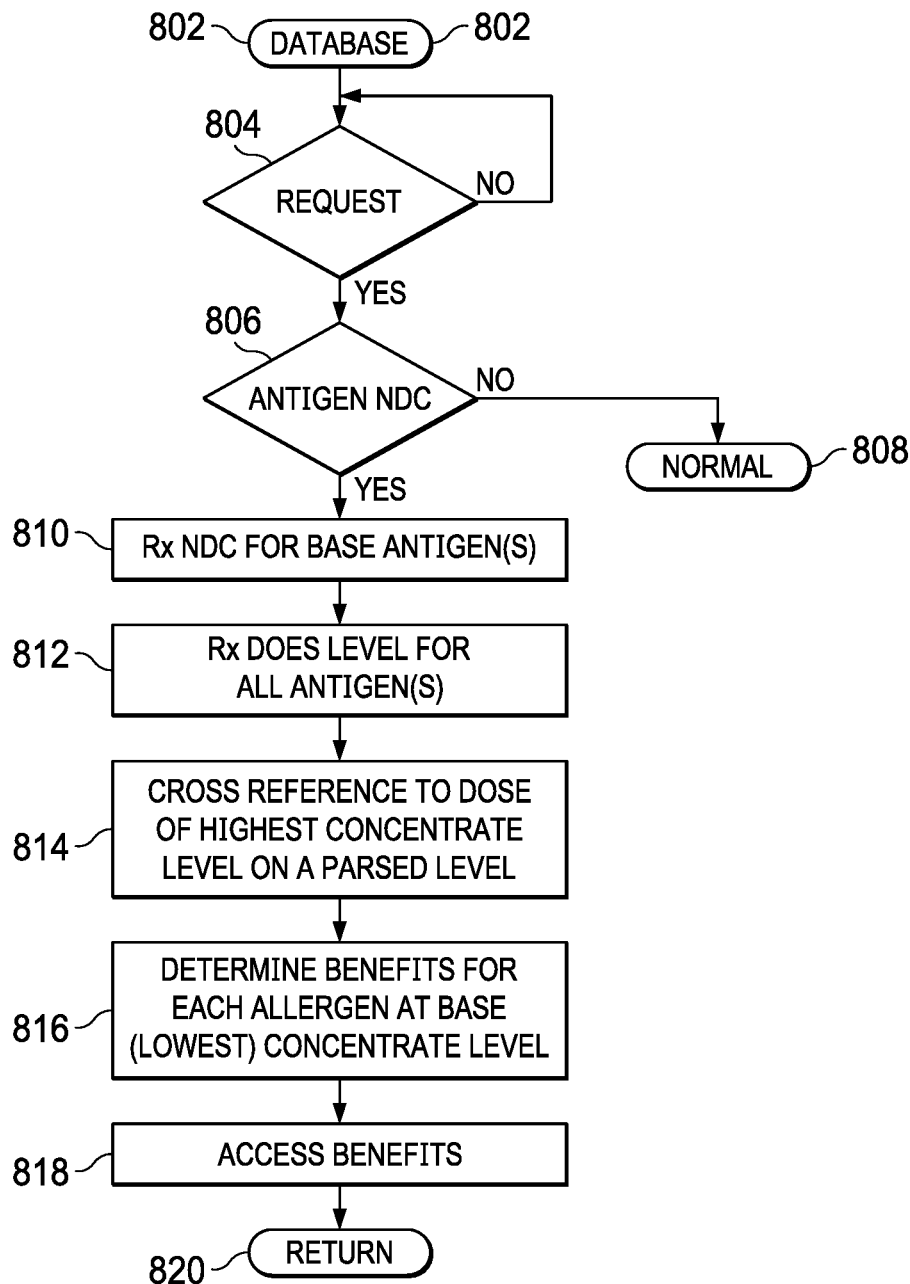
FIG. 8 illustrates a flowchart for interfacing with database for accessing benefits by the pharmacist.

Referring now to FIG. 8, there is illustrated a flowchart depicting the operation of accessing the database, which is initiated at a block 802 and then proceeds to a decision block 804. The decision block 804 determines whether a request for access has been received and, if so, the flowchart proceeds to a block 806 to determine if the particular request of the PBM database is associated with that for an antigen. If not, the program will follow the "N" path to a block 802 to proceed along the normal benefit determining process. This is not described herein. If, however, the request is for an antigen, this is a specific operation, since the only NDC that exists is for a base concentrated antigen that is too toxic to be directly distributed to a patient or for another dosage level that is to be diluted. Once an antigen NDC is indicated, the program flows to a block 810 in order to receive the NDC for the base antigen or antigens and then to a block 812 to receive the dose level for all of the antigens, as well as the carrier and the dilution procedure that is utilized. The program will then flow to a block 814 in order to cross reference the particular dose level that was actually distributed to the patient to the dose of the highest concentrated level of the base concentrate material. This will be on a parsed operational level. This parsed operational level means that, for example, if 10 antigens were distributed in a cocktail, it would be necessary to cross reference the distribution of this particular dosage level to the actual material utilized from the NDC-carrying base concentrated level. If, for example, for a single base concentrated material that yielded an antigen in the cocktail mixed, required 1 mL out of a 50 mL bottle, the benefits for that one milliliter could be determined, as this is a "dosage" of the base concentrated level that is associated with an NDC. As indicated by a block 816, the benefits can be determined for "each" allergen at a base or lowest concentrated level that is associated with an NDC. It is noted that an NDC might be provided for an already diluted level of a particular antigen. However, it is always necessary to determine what portion of the NDC-carrying material is utilized down to the final diluted level and then cross correlate this back to the NDC-carrying material at its particular dilutant level, this requiring some information as to the procedure for dilution, the carrier, etc. in order to adequately determine exactly how much of the NDC-carrying material was utilized. The program then proceeds to a block 818 to then access the benefits and then to a block 822 to end program.

Figure 9:
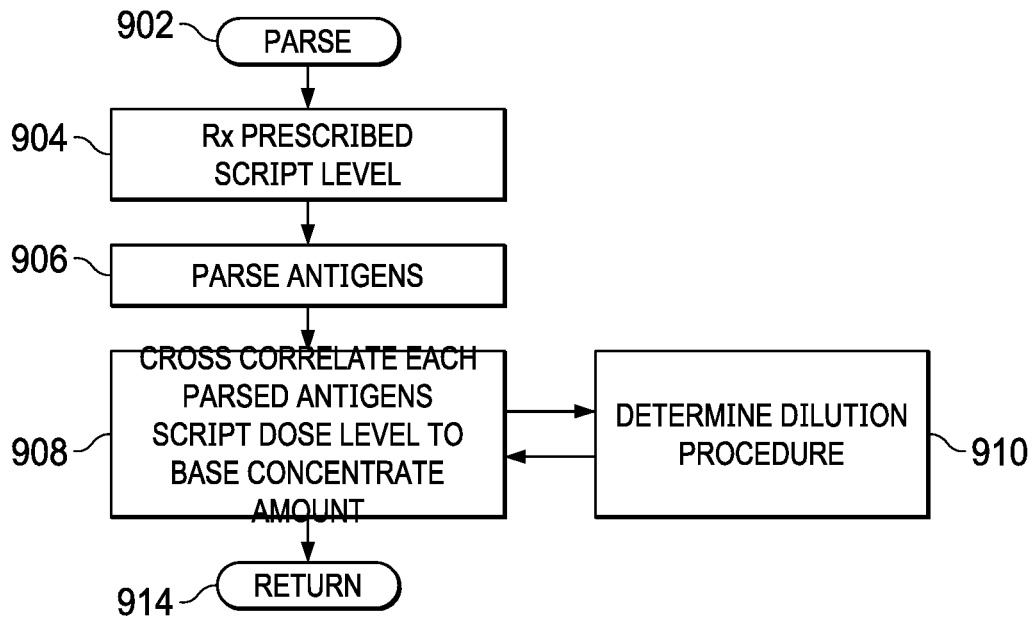
FIG. 9 illustrates a flowchart for the parsing operation at the database for parsing non-NDC allergens to an NDC-bearing base concentrated allergen.

Referring now to FIG. 9, there is illustrated a flowchart for the parsing operation, which is initiated at a block 902. The program then proceeds to a block 904 in order to receive the prescribed script levels. The program then proceeds to a block 906 in order to parse antigens in the cocktail to individual antigens (noting that a single antigen could be provided for). The program then flows to a block 908 in order to cross correlate each of the parsed antigens and the script dose level back to the base concentrated amount, noting that this requires the carrier to be known, the procedure to be known for dilution. Since the script merely states that the most diluted level must be provided for, the pharmacist then to provided that particular antigen. The particular base concentrated antigen could be at different concentrated levels which would require a pharmacist to utilize one of multiple dilution procedures to obtain the final diluted level desensitization regimen. However, as described hereinbelow, it could be that the physician prescribes a particular antigen in the cocktail that can be found in a deliberate antigen at a base concentrated level that contains multiple antigens. This is very common in the industry. For example, some companies deliver already mixed cocktails for various types of pollen. If the physician only prescribed one out of these types of pollen, within this procedure it must be noted so that the particular amount of base concentrated material that can be reimbursed based upon its NDC could be allocated. For example, if it were determined that 1.0 mL of the base concentrate pollen cocktail is required in order to get the prescribed amount of the one type of pollen, and this was from a 50 mL bottle, this would indicate a 1 mL dosage of the base clustering level, but this would be divided by the number of particular antigens that are in the base concentrate material. If there were, for example, ten antigens contained in the cocktail, then this would be divided such that only 1/10 of the dosage would be applied to benefits. That is, a 50 mL bottle to be considered as containing, assuming that the starting dosage is always 1 mL or any deleting process, as having 500 dosages of individual antigens. This, of course, requires knowledge of the dilution procedure, as indicated by a block 910. Once the crosscorrelation is complete, the program proceeds to a return block 914.

Figure 10:
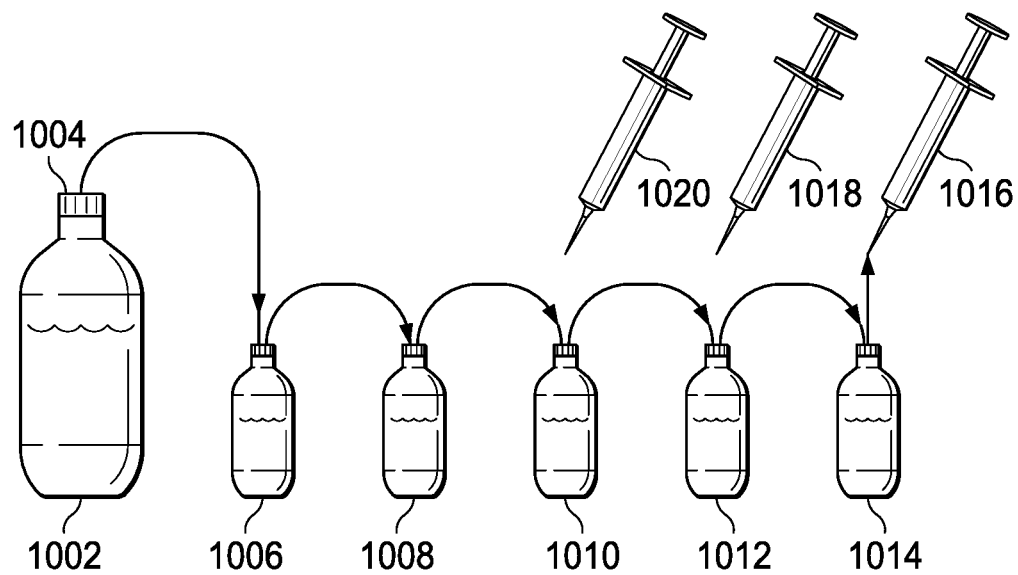
FIG. 10 illustrates a diagrammatic view of a dilution sequence of diluting a concentrated antigen extract.

Referring now to FIG. 10, there is illustrated a depiction of a technique for diluting immunomodulators such as antigens, as one example. Preparation of a diluted antigen is performed first by receiving a bottle of extract concentrates at a base concentrate level from an approved vendor. These are formulated in a given weight/volume (w/v) format with a given antigen associated therewith. For typical antigens such as those associated with the cat antigen, these are relatively well controlled. Typically, a vendor will provide an extract for a single antigen or allergen. Allergens such as pollen and the such are not as well controlled due to the technique for collecting such. In any event, there are typically very few approved vendors for these extracts and an allergist typically receives these vendor provided concentrates in a sufficient quantity to make the necessary diluted solution.

Allergen extract is typically comprised of a non-allergenic material, a non-allergenic protein and an allergenic protein. The extraction solutions can be aqueous containing saline and phenol or could be a glycerinated solution. The allergen is added, the units of measure are sometimes referred to as "AU" for "allergy units," typically used for mites. These are referred to as "AU/mL." For such things as grass and cat, the term "BAU" is used for "bioequivalent units." For other allergens, the terminology is, for example, 1:20 w/v, which stands for 1 g source material per 20 mL of fluid. The relationship between BAU and 1:20 w/v depends upon the extract. In any event, there is a defined amount of extract contained within the concentrate.

When concentrated extracts are formulated by an authorized vendor, they are typically provided in standardized versions and non-standardized versions. In standardized versions, they typically are provided in a 50% glycerin dilutant. They can either be a single allergen extract or they can be a mix. For example, one can obtain a "9 Southern Grass Mix (concentrate)" which contains equal parts of: 2 Bermuda at 10,000 BAU/mL, P27 7 Grass at 100,000 BAU/mL, 15 Johnson at 1:20 w/v. For non-standardized extracts, these are typically provided in either a glycerin dilutant or an aqueous dilutant such as saline. They can be a single extract or a mix. Thus, whenever a concentrated extract is referred to hereinbelow, this refers to a formulation that is provided by an authorized vendor that can be diluted in accordance with the processes described hereinbelow. These are typically provided in the 50 mL bottles with a needle compatible.

Referring back to FIG. 10, the extract concentrate is disposed in a bottle 1002. This is a sterile concentrate that has an injection stoppered top 1004. There are provided a plurality of five 5 mL sterile injection stoppered bottles 1006, 1008, 1010, 1012 and 1014, although there could be more and the bottles or containers could be larger than 5 mL. Each of these bottles has disposed therein a defined amount of dilutant, depending upon what the final requirement may be. Typically, the amount of dilutant is 4.5 mL. The procedure is to, first, extract a defined amount of the concentrated extract from the bottle 102 and dispose it in the bottle 1006. This is facilitated by the sterile hypodermic that is inserted through the stopper at the top of the bottle 1002 to extract concentrate and then the hypodermic is inserted to the stopper in the bottle 1006 to inject extract from bottle 1002 into bottle 1006. Typically, the concentration in the concentrated extract bottle 1002 is 1:20 w/v. This will result in a dilution of 1:10 in bottle 1006. If the amount injected is 0.45 mL. Then, 0.45 mL of the diluted solution from bottle 106 is then extracted and inserted into bottle 1008, resulting in a 1:100 dilution of the original concentrate in model 1008. The process is repeated up to the bottle 1014 to provide a solution that is at a dilution of 1:100,000 of the original concentrate. This is a conventional way to provide a selected dilution of the original antigen. However, it should be understood that any concentration level can be provided from one bottle to the next. The purpose of using the sequential bottles is to allow an achievable portion of one bottle to be distributed to the next bottle, rather than trying to extract a very small amount of the initial concentrated extract. Typically, an allergist will then extract from the desired dilution an amount of the diluted antigen for injection percutaneously. Typically, desensitization is achieved by using the most diluted antigen level initially and sequentially moving up to a higher concentration level over time 1.

Illustrated in FIG. 10 are three hypodermic needles, one selecting a "dose" from bottle 1014, and labeled hypodermic 1016, a second hypodermic needle 1018 for retrieving a dose from bottle 1012, a third hypodermic needle 1020 for extracting a dose from bottle 1010. Each of the hypodermic needles 1016, 1018 and 1020 will contain a different diluted dose. These would typically be separate needles in the event that the allergist or medical professional is injecting a patient. For other purposes, they could be the same needle, depending upon the dose or concentration required. A "dose" is defined by the amount of all the diluted product that would be required for the desired immunotherapy. This is defined by the medical professional. If, for example, bottle 1012 were utilized, it may be that 1 mL of diluted solution constituted a "dose." It could be that less than 1 mL constituted a "dose."

This entire procedure is provided as a "data" procedure which can be designed for particular carriers and the such. Additionally, the carrier could be a transdermal cream which could be mixed by the pharmacist. Any carrier that is able to contain one or more diluted antigens at any prescribed dilution level can be utilized.

Referring now to FIG. 11, there is illustrated a process flow for the embodiment of FIG. 10. This is initiated at a process block 1102 and then proceeds to block 1104 wherein a certain amount of concentrated extract is received from a vendor, this being a qualified or authorized vendor for the extract. This is typically at a predetermined concentrate level of, for example, 1:20 m/v. The process then flows to a block 1108 wherein a defined quantity of, for example, 0.45 mL is transferred to a 5 mL bottle which already has a quantity of 4.5 mL buffered saline solution disposed therein. The process then flows to a block 1110 to determine if this was the last dilution step needed, as described hereinabove, depending upon what level of dilution is necessary. If, for example, five steps of dilution are required for a particular patient, then all five steps would be processed. However, it is not necessary to do all five steps if an intermediate dilution is required. This essentially customizes the overall operation for a particular patient. Further, the industry is so regulated such that only 5 mL bottles can be utilized for this dilution process. Thus, it will only be a maximum of 5 mL of diluted material available at any step prior to proceeding to the next step. Thus, if all 5 mL are required, then the next step is not desired or useful. If it is not the last dilution step, the process flows to a block 1112 to extract 0.45 mL of diluted antigen from the current 5 mL bottle and then flows back to the input of the process block 1108 after incrementing the bottle count at a block 1114. This continues until the last dilution, at which time the process flows from the block 1110 to a terminate block 1116. Again, any type of carrier could be utilized and bottles larger than 5 mL could in fact be utilized. This all depends upon the number of "doses" at a particular diluted level that are required by the physician right the initial script or prescription.

Referring now to FIG. 12, there is illustrated in overall flow of the operation of moving concentrated antigen from a vendor to an end user via a pharmacist. As noted hereinabove, the liquid antigen in a concentrated extract at the base concentrate level that has associated therewith an NDC was first received from a vendor that assigned that NDC, which is basically a combination of a single antigen or antigens suspended in a sterile agent. This is indicated by a block 1202. The antigen is then diluted by the pharmacist from this extract to a desired diluted level, as indicated by a process block 1204. This is combined in a block 1206 with a sterile carrier and containment material, i.e., sterile saline solution or, even a transdermal cream, for distribution to a patient. This, as described hereinabove, will typically be a defined number of doses of a single diluted antigen or multiple diluted antigens, wherein a dose is again defined as being a typical dose that a medical professional would administer to a patient in an office visit necessary to achieve a therapeutic result for which a patient could administer to themselves. This is either transferred as a combined antigen (diluted)/encapsulation product for storage on a shelf, as indicated by a block 1212, or it would be transferred to a medical professional for a patient for management and disposition.

Referring now to FIG. 13, there is illustrated a diagrammatic view of three different extracts of antigens/allergens 1302, 1304 and 1306. Each of these is for a particular antigen or allergen. The first two are for antigens respectively associated with a cat and a dog. The third is for an allergen associated with pollen. They are each diluted in accordance with the process described hereinabove with respect to FIG. 10. As illustrated, the antigen extract in bottle 1302 is transferred as a diluted level to either an encapsulation material in a container 1310 or 1312, each at a different diluted level. This is similarly the case with respect to the antigen in bottle 1304 and the allergen in 1306 wherein the diluted level of the antigen in the bottle 1304 is disposed in containers 1314 and 1316 and the diluted level of the allergen in bottle 1306 is disposed in containers 1318 and 1320. Typically, any extract will be 100% pure with respect to the particular extract. These concentrated extracts are not typically mixed, which is typically a function that the medical professional or compounding pharmacist will perform. This, of course, is a customized mixture for a particular patient, i.e., this is a patient-specific combination as defined by the medical professional in the script provided to the pharmacist. For storage on the shelf, the operation of FIG. 13 will be facilitated in order to ensure that the containers 1310-1320 contained only a single antigen. Thus, when transferring the container to a store, for example, this would be stored on the shelf as a single allergen combination of the base concentrate level.

Referring now to FIG. 14, there is illustrated an alternate disclosure to that of the embodiment of FIG. 13. In this embodiment, each of the immunomodulators or antigens at the concentrated levels in the bottles 1302-1306 are diluted in accordance with the process noted hereinabove wherein they are sequentially diluted in the associated 5 mL bottles. However, note that only a maximum of 5 mL can be extracted from a given bottle at the last dilution level. If, in this example, it is desired to distribute a predefined number of doses to a final carrier 1402 having a fixed amount of carrier such as saline disposed therein and each dose will add to that material provide the final overall dosage or, alternatively, a viscous transdermal cream can be utilized that is initiated at an original fixed value in grants such that each dose will be associated with a single gram of that transdermal cream material, and then the amount of diluted antigen must be adjusted such that single dose is contained within 0.3 mL of the material. Thereafter, if 3 mL of antigen is extracted from a given bottle, this constitutes 30 doses such that a single dose will be associated with a single dose of the final encapsulation material. In this example, from each of the last dilution bottles for each of the concentrate bottles 1302-1304, 3 mL is extracted and inserted within the container 1402 containing prescribed level of carrier material, be that saline solution or a transdermal cream. Thus, for each milliliter of saline solution, for example, or each gram of transdermal cream material, there will be a single dose of the particular antigen associated there with. Thus, the carrier material in the container 1402 now acts as a consolidator of all of the antigens for a cocktail.

Referring now to FIG. 15, there is illustrated a flowchart depicting one example of the generation of a script for a single antigen and filling of that prescription based on that script and getting reimbursed therefor. This is initiated at a block 1502 and then proceeds to a block 1504 in order to prepare the physician script for a single antigen. The program then flows to a block 1506 in order to define the requirements of the maximum dilution for the initial desensitization. The physician defined at which level the script is written for. For example, the physician sets forth a regimen. This regimen defines six levels of dilution, each level of dilution are required for a predetermined amount of time. For example, the most diluted level might be required to be administered in three doses per week for three weeks for total of nine doses. The first script would require the pharmacist to deliver to the patient a file containing nine doses at that diluted level of the at least a single antigen. The physician could then require the second higher level to be provided over the course of one week at three doses per week. This might require a second script to be filled by the pharmacist or, alternatively, the pharmacist could fill that script that same time and maintain that particular vial on the shelf for distribution to the patient at a later time, all of this depending upon the script provided by the physician. Of course, the physician could require the patient to come into the office for observation and then write another script. This would be a separate and distinct operation and prescription which would be independently associated with a different set of benefits possibly.

After the dilution level is determined for the initial desensitization or at any level in the desensitization regimen, the program flows to a function block 1508 wherein the pharmacist selects concentrate antigen and then goes to the dilution process required order to achieve the desired diluted level. The program then proceeds to a function block 1510 where in the pharmacist enters the NDC code for the base concentrate level and the script level. Basically, what the pharmacist does is enter the antigen name and the dosage level provided by script. The program then proceeds to a function block 1512 in order to perform a lookup in the PBM database for the particular antigen that is associated with the script. This lookup does a correlation, as will be described hereinbelow, to the lowest concentrate level having an NDC for that particular antigen. Knowing the dilution level and the procedure, it is possible to determine what amount of the NDC-carrying concentrate level for that particular antigen was utilized and then a reimbursement obtained and four. This is indicated by the function block 1514 and 1516. The program then flows to an initial End block 1518.

Referring now to FIG. 16, there is illustrated a table for a single antigen and the overall crosscorrelation information. This is a relational database. In this table can be seen that there is provided a column for the NDC code which is populated for a particular antigen. This indicates the name of the antigen and also information associated therewith. There is also a dilution procedure for multiple procedures that can be associated with administering this particular antigen. Since the NDC code associated only with the type of antigen but also the concentration levels, this will be associated with the dilution level to determine what the various dilutant levels are in the overall standard process. As noted, the base level is indicated by a dilutant level D1 or a base concentrate level there than provide five additional dilutant levels D2 through D6. Each one of these dilutant level columns has associated there with a particular range of dilutant levels. As indicated by example, there are levels 1 through 3 for each of diluted levels, with more possible. Therefore, if the most diluted level, D6 were selected and that the procedure required that the dilutant level Z6 for the dilutant level column D6 were selected as the N dilutant level that was required by the physician in the script provided to the pharmacist, this would be what was put into the PBM system. However, there is no NDC associated with this particular antigen at this particular dilutant level. Therefore there must be some crosscorrelation back to column D1 for the base concentrate level, which column has an NDC associated therewith. If the final dilutant level was Z6, this could be cross correlated back within the same road to the dilutant level Z1 of the base concentrate. However, although not shown, there could actually be multiple roads associated with the dilutant level Z6, one for each dilution procedure. Thus, the crosscorrelation from the dilutant level back to amount of base constitute antigen required to process through the diluting procedure requires knowledge of the diluting procedure. This is illustrated in FIG. 16A, wherein each column for the dilutant level Z6 has three has such that there are provided three different amounts of the base extract that would be required, Z1, Z2' and Z". For example, it might be that this requires corresponding levels of 0.8 mL, 1.0 mL or 1.1 mL for those three different levels in order to accommodate the three different dilution procedures S1, S2 and S3. Thus, it is not just a mere crosscorrelation operation but, rather, and overall knowledge of the process that is required in order to determine how much actual product was utilized of the original base NDC-carrying antigen. Only when the amount of the base concentrate NDC-carrying antigen that is utilized is known can the actual dosage be determined. For reimbursement purposes, it is important to know whether 0.8 mL, 1.00 mL or 1.1 mL was use of the base concentrate NDC-carrying antigen is utilized. Reimbursement is calculated based upon this. However, all that is necessary for the pharmacist to do is to put in the end product that was generated and the procedure for coming up with that end product and relate that to the antigen that was utilized.

Figure 15:
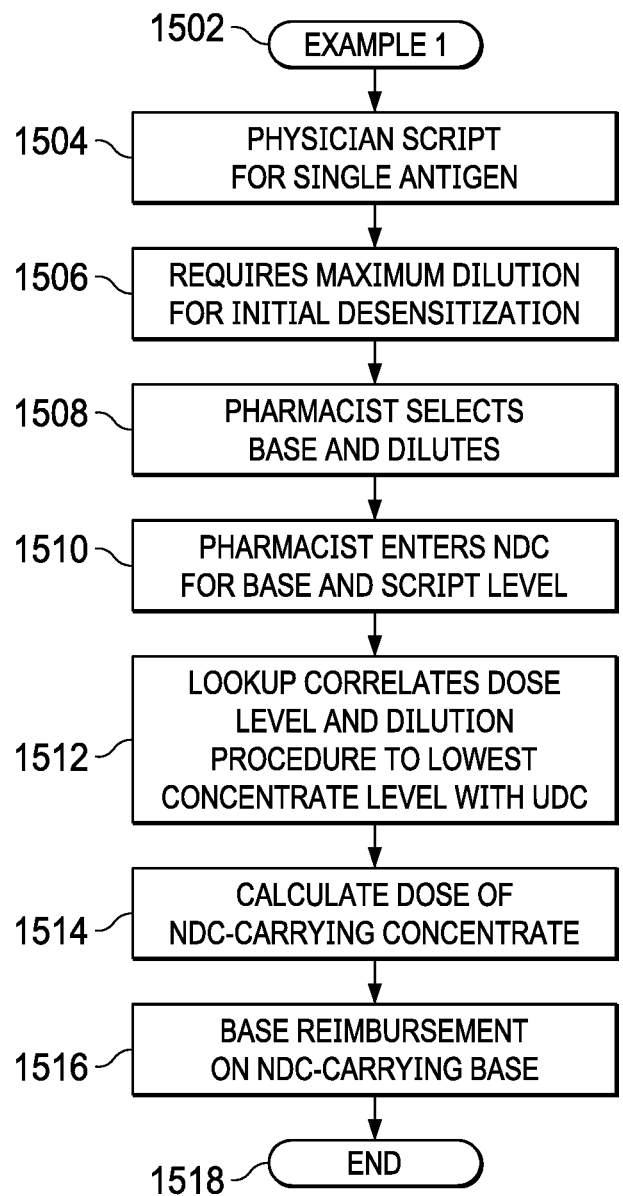
FIG. 15 illustrates a flowchart for one example of processing a physician script.
Figure 17:
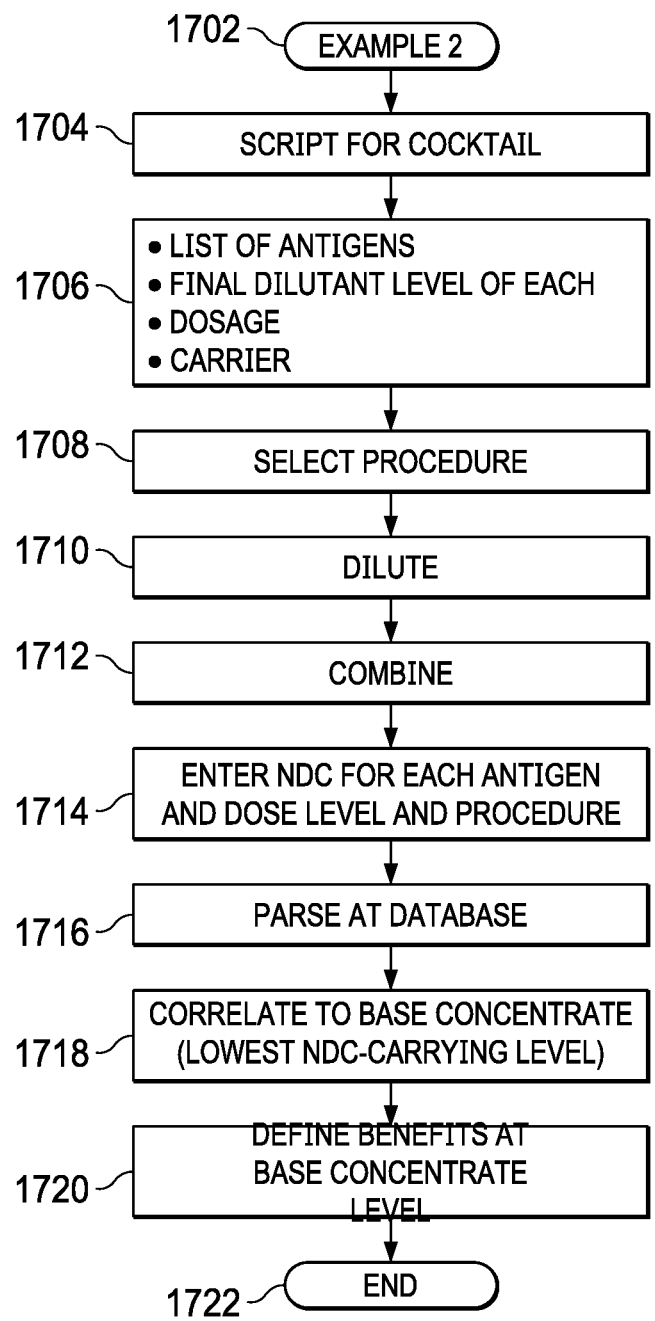
FIG. 17 illustrates a second example of that illustrated in FIG. 15.

Referring now to FIG. 17, there is illustrated a flowchart for a second example for preparing a script for a cocktail, which is similar to the flowchart of FIG. 15. This is initiated at a block 1702 and then proceeds to a block 1704 to generate a script for a cocktail which is a patient-specific cocktail based upon a prick test performed. This is unique to that patient for that particular time. The program then proceeds to a function block 1706 in order to provide in that script a list of the antigens to be placed into the cocktail by the pharmacist, the final dilutant level of each, the dosage and the particular carrier. The program then flows to a function block 1708 in order to select the procedure that the pharmacist will utilize to provide this final diluted product with the prescribed number of dosages. This might be prescribed by the position or it might be selected by the pharmacist. The program then flows to a function block 1710 wherein the pharmacist performs the dilution operation and then combines various antigens into the cocktail, at a block 1712. The program then proceeds to a function block 1714 wherein the NDC for each antigen is entered into PM database, the dose level and the procedure. The program then proceeds to a function block 1716 to parse the particular antigens at the database, this parsing required in order to process each antigen in the database separately, as there must be a crosscorrelation back to each individual antigen, since only each individual antigen has an NDC associated there with. The program then proceeds to a function block 1718 in order to correlate the antigen back to the lowest concentrate NDC-carrying level, as described hereinabove with respect to the embodiment of FIGS. 15 and 16 and then to a function block 1720 in order to define the benefits and then to a function block 1722 in order to end the program, after the cocktail has been distributed to the end user such as the patient or the medical professional.

Figure 13:
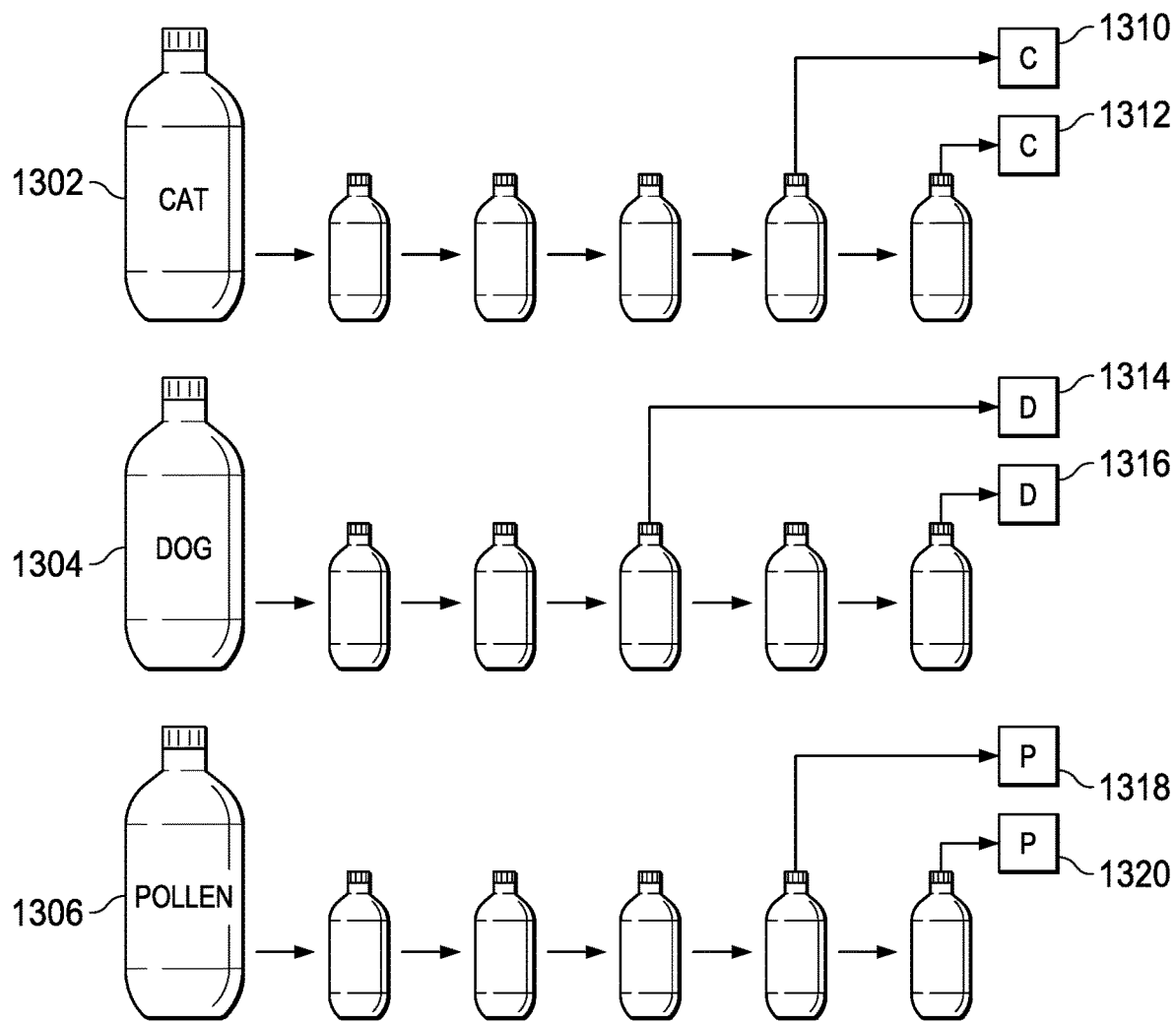
FIG. 13 illustrates a process flow for multiple extracts.
Figure 14:
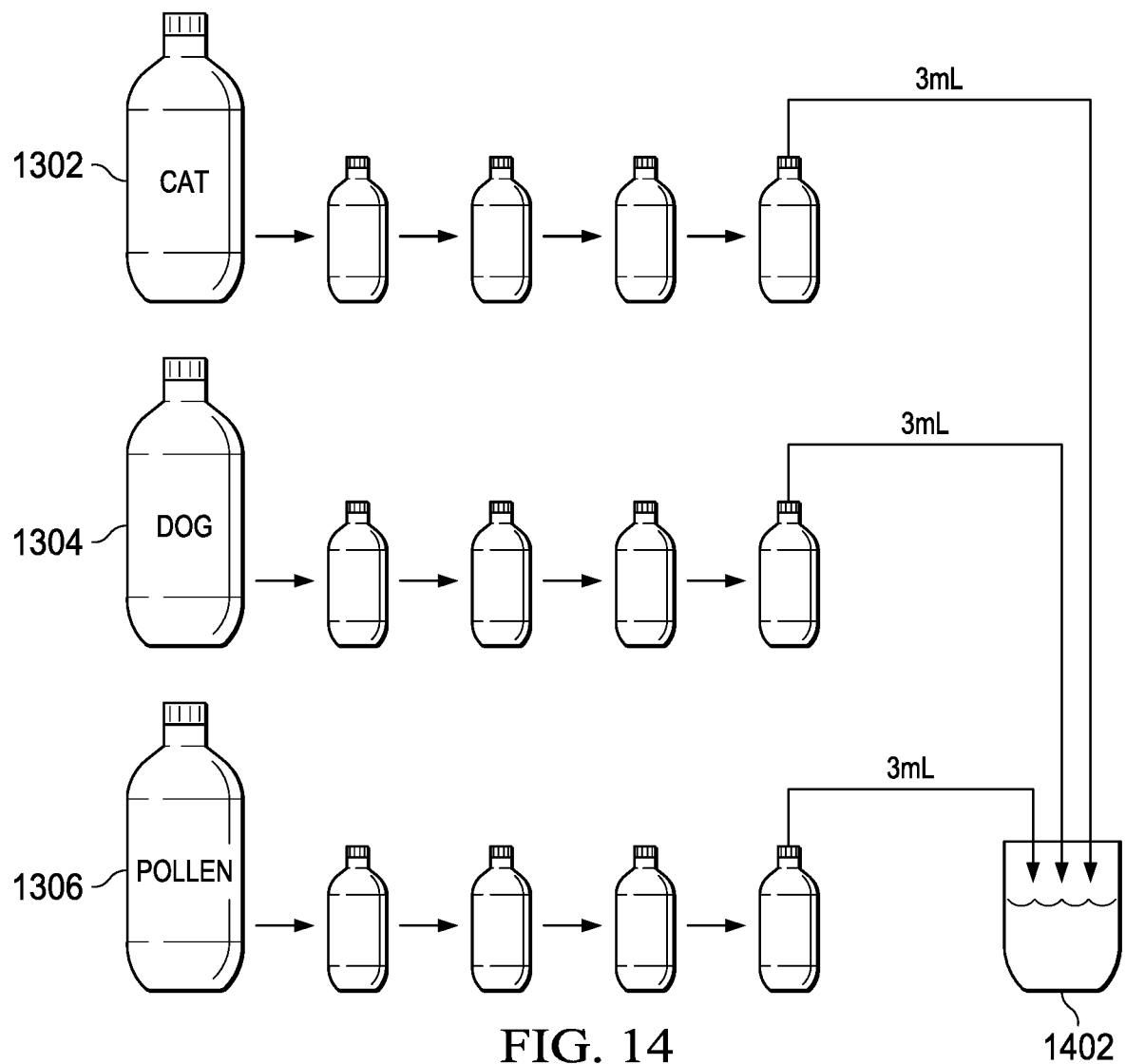
FIG. 14 illustrates an alternate embodiment of FIG. 13.
Figure 18:
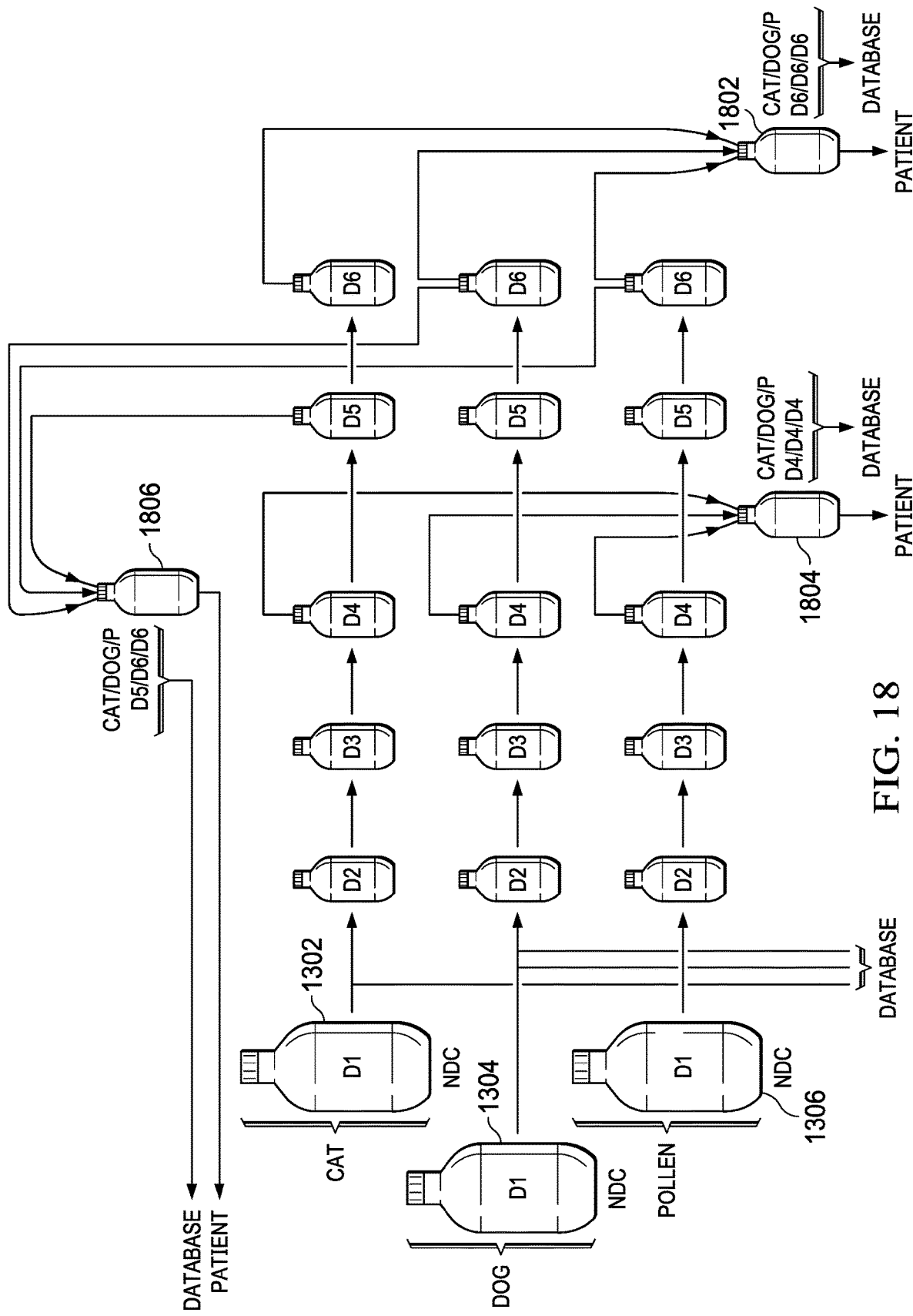
FIG. 18 illustrates a diagrammatic view of processing of a script received from a physician at a pharmacist to compound a patient-specific dosage.

Referring now to FIG. 18, there is illustrated a process, which is similar to that described hereinabove, for creating a cocktail from three different base concentrate antigens 1302, 1304 and 1306, referring hereinabove to the description with respect to FIG. 13. These are diluted down in five separate steps to a final dilution level D6. In a first operation, there is provided a final vial 1802 that receives the final dosage from each of the processes for diluting the initial base concentrate levels. It may be that each of the final vials D6 each have 5 mL contained therein. By containing no carrier material in the final vial 1802, 3 mL of each of the extract can be placed therein resulting in a vial with 9 mL therein. If the physician prescribed the regimen to deliver a 1 mL dose of this concentrated level III times per week for three weeks, this would require nine doses and thus 9 mL of the cocktail. This overall process, for example, would require the pharmacist to understand each step of the dilution process to arrive at the final diluted level. Thus, the pharmacist would indicate that there were three antigens in the final vial 1802 and that they were at the concentrate level D6/D6/D6. This would be provided to the PDM database. With this information alone, the system at the PDM database can cross correlate this back to the exact amount of base concentrate level lies for each of three base concentrate antigens 1302, 1304 and 1306 utilized.

Alternatively, there is provided a vial 1804 which is the result of a different selection of cocktails from the D4 level. This, again, would have three antigens in the concentrate level D4/D4/D4. This would again be provided to the PDM database which would then, based upon the dilutant level for each of the antigens and the procedure utilized to achieve that dilutant level to relate this back to the antigens utilized at the NDC-carrying concentrate level. If, for example, this vial 1804 resulted in 9 mL of material but the physician only required three doses of 1 mL each for two weeks, this would only require 6.0 mL. The pharmacist might only dispense 6 mL out of the 9 mL to the patient or professional. Even though the doses distributed are 6.0 mL, this 6 mL of final product of D4/D4/D4 of Cat/Dog/Pollen antigen has to be related back to the original antigen value.

In an alternate embodiment, there is a vial 1806 provided that has been provided where in it receives diluted antigens from slightly different and vials. In this operation, the three antigens are D5/D6/D6 and this is provided back to the PDM database. Of interest is that all three vials 1802, 1804 and 1806 will each the input to the PDM system with their procedure and the result will be that, for this example specifically, at the reimbursable be the same, as the starting dilutant will be identical. This is procedure specific and script specific, with the cocktail noted as being patient-specific.

Figure 19:
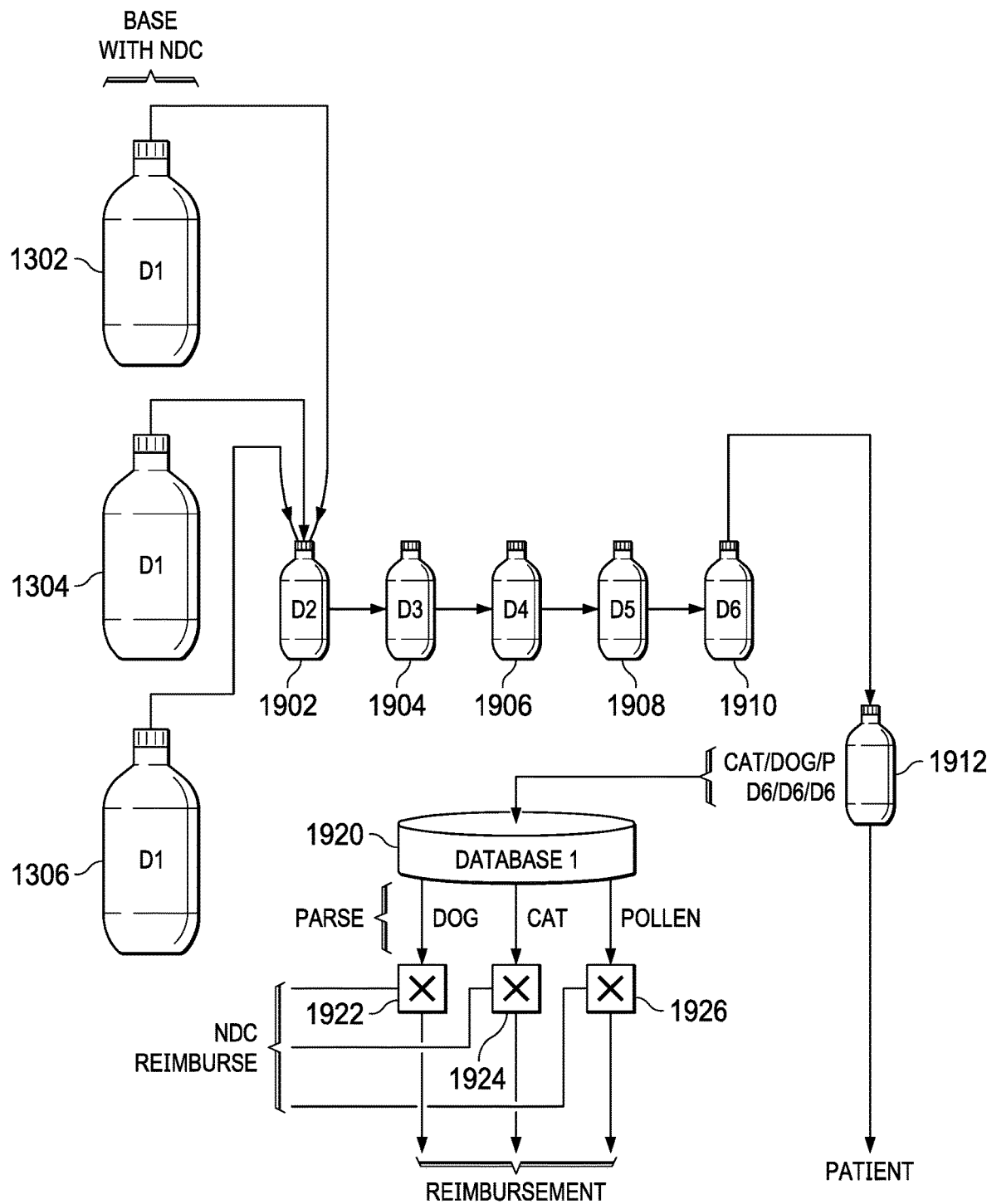
FIG. 19 illustrates an alternate embodiment of that illustrated in FIG. 18.

Referring now to FIG. 19, there is illustrated an alternate embodiment wherein each of the base antigens 1302, 1304 and 1306 are subjected to a different procedure wherein each of the original starting amounts are input to a first diluting vial 1902 and are subsequently diluted through vials 1904, 1906, 1908 and 1910 to a final vial 1912. This is an distributed to the patient. This final vial represents the dilution at the vial 1910, which is D6/D6/D6. This, along with this procedure is then transferred to the PDM database, as indicated by block 1920, which is then parsed to the specific antigens and into a translator associated with each antigen, indicated by a "X" for the crosscorrelation operation, blocks 1922, 1924 and 1926 associated with the Dog, Cat and Pollen antigens which will then define the reimbursement. Each translation block 1922 will be associated with a reimbursement database for defined benefits associated with the particular antigen. Of course, it is important to know the amount of antigen that was actually utilized in the overall procedure which, again, requires knowledge of the final script dilutant level of the antigen delivered to the patient and procedure for obtaining that diluted level.

Figures 20A, 20B:
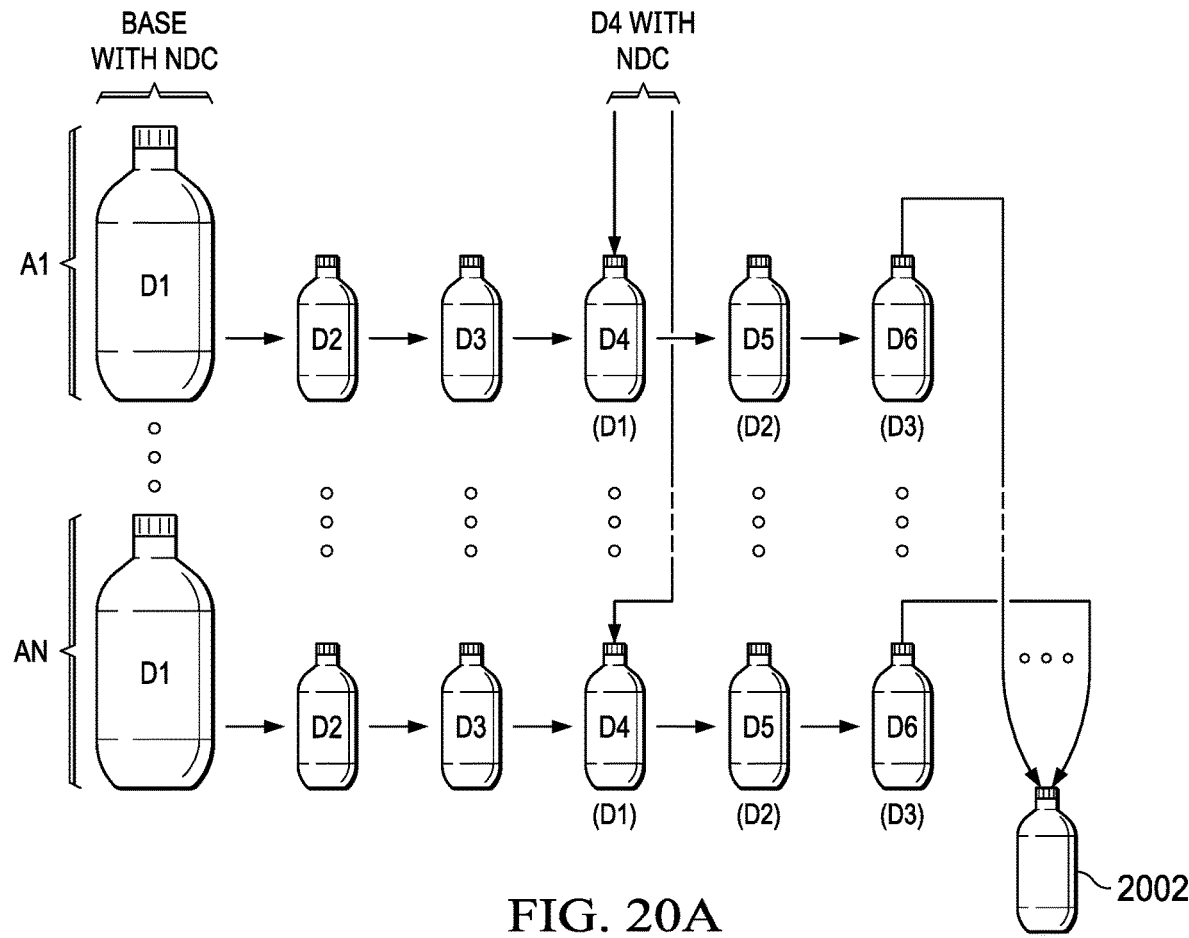
FIG. 20A illustrates a diagrammatic view of a process of filling a script received from a position and FIG. 20B illustrates a table associated with such process.

Referring now to FIG. 20A, there is illustrated a diagrammatic view of an overall process wherein the NDC is associated with an intermediate level of dilutant. In this embodiment, the dilutant level D4 is illustrated as having an NDC associated therewith, as well as the base concentrate level. Thus, it is possible that the reimbursement can be defined back to this intermediate concentrate level. This is indicated in a table in FIG. 20B, wherein the table can have associated with original diluted levels D4, D5 and D6 crosscorrelation relationships with respect to the base concentrate level but, in this table, there are only three diluted levels required, the dilutant level for vial D4, the vial D5 and the vial D6. If the concentrate level at the final vial was X3 based upon the NDC code being at vial D4, all that would be required is to do a crosscorrelation back to the dilutant level required from the file D4. This would be for each of the dilutant set was combined in a vial 2002 from each of the antigens in the script, this indicated as being the antigens A1-N.

Figure 21:
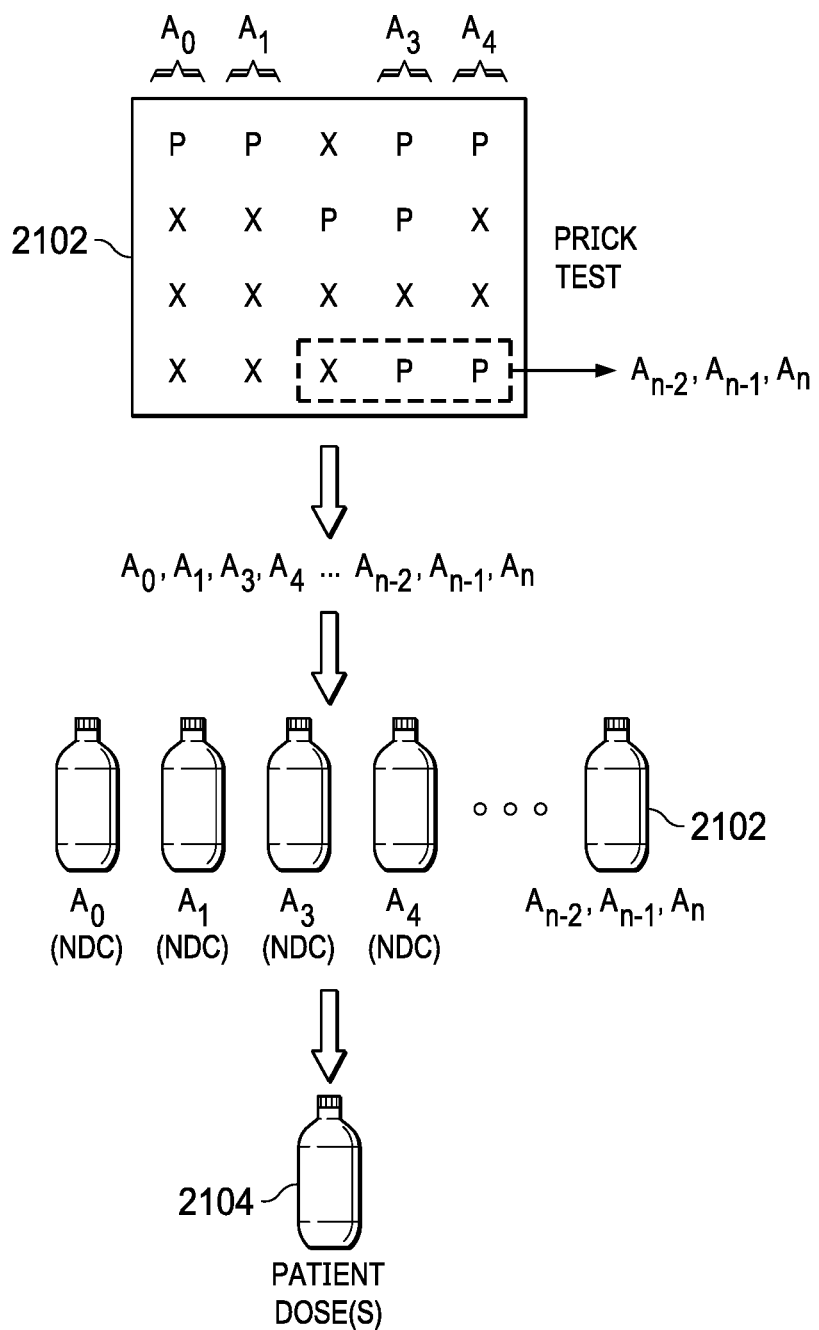
FIG. 21 illustrates an overall process flow illustrating the prick test, the script flowing through to the final patient does.

Referring now to FIG. 21, there is illustrated a process for mapping a prick test to the script. As illustrated, there is provided a diagram of the prick test, indicated by a reference numeral 2102. This diagram 2102 indicates the locations of the particular allergens that were administered to locales on the person of the patient. This diagram illustrates the results with a "P" indicating a positive reaction and that an "X" indicating a negative reaction. Thus, the "P" indicates a sensitivity that must be considered in the script. Of interest is that the particular manufacturers of antigens might have a cocktail already existing in the base concentrate. This is illustrated with the bottom three test associated with antigens A(n–2), A(n–1) and AN. These are the last three antigens in the list. Of these, the last two are positive and the third for the last is negative. However, the script will have to include only the last two for the patient-specific script but the pharmacist only has the cocktail of all three available to them. Thus, the script will have a A0, A1, A3, A4 . . . , A(n–1) and AN as the antigens that are required for the desensitization regimen. This will be provided to the pharmacist which will then select NDC-Kerry antigen bottles A0, A1, A3, A4 . . . , And finally a bottle 2102 containing A(n–2), A(n–1) and AN, wherein only A(n–1) and AN are required in script to fill the prescription. This is then processed to provide the final patient dosage in the cocktail in the vial 2104.

Figures 22A, 22B:
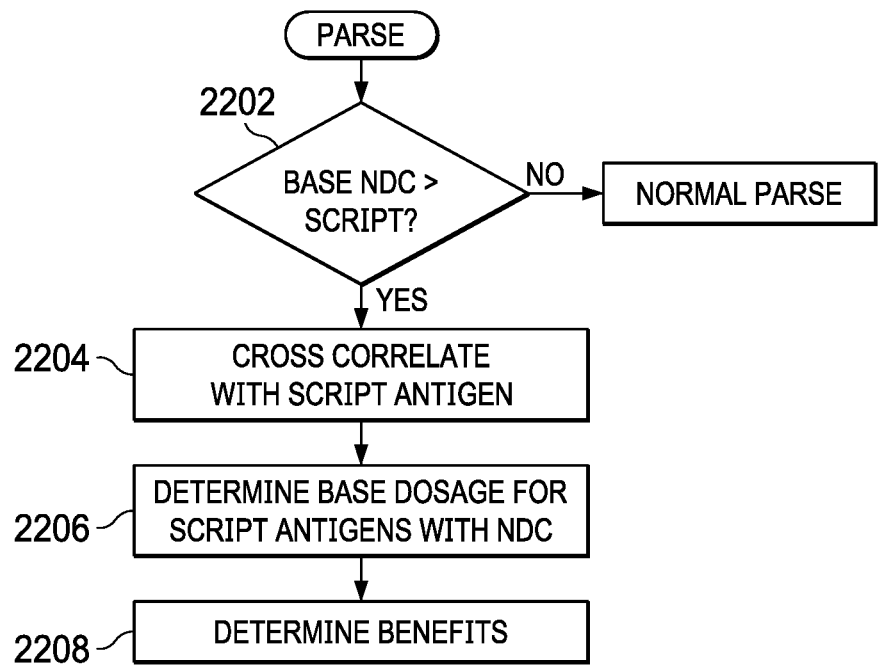
FIG. 22A illustrates a flowchart for parsing an antigen having a base dose with more than the prescribed antigens and FIG. 22B illustrates a table associated with the parsing operation.

Referring now to FIG. 22A, there is illustrated a flowchart depicting the overall parsing operation before the operation of FIG. 21A. In this operation, if the base NDC has a greater number of antigens than the script, a decision block 2202 will determine such and flow to a block 2204. The program will then flow to a function block 2206 in order to determine the basis dosage for the script as required by and set forth by the position of the antigens with the particular NDC, even though that NDC is associated with more than the antigens required by the script. The program then flows to a function block 2208 in order to determine the benefits. This is illustrated best with respect to the table of FIG. 22B. Here, it is illustrated that there are three procedures for providing the end dilutant level at the vial D6 for each of the antigens in the cocktail antigen vial 2102. If a certain amount of antigen is extracted from this particular vial 2102, it will contain all three antigens. At a particular concentrate level at the level D6, this will yield the necessary concentrated level of the two antigens desired even though the third antigen is included. Since the final dilutant level is known for the two prescribed antigens, they can be cross correlated back to the amount of antigen that was actually extracted. However, for example, if 3 mL of the extract in vial 2102 were extracted, this might represent a particular portion of a 100 mL bottle and, if all three antigens have been prescribed, this would be the basis for the reimbursement. However, if only two antigens were prescribed, only two thirds of that prescribed extract would be reimbursed. Thus, by utilizing known script at the known dilutant level, this can be cross correlated back via the standard procedure (or whatever procedure is utilized) to what was actually utilized of the NDC-carrying base concentrate material to actually derive the final prescribed and delivered antigen to the patient.

Figure 23A:
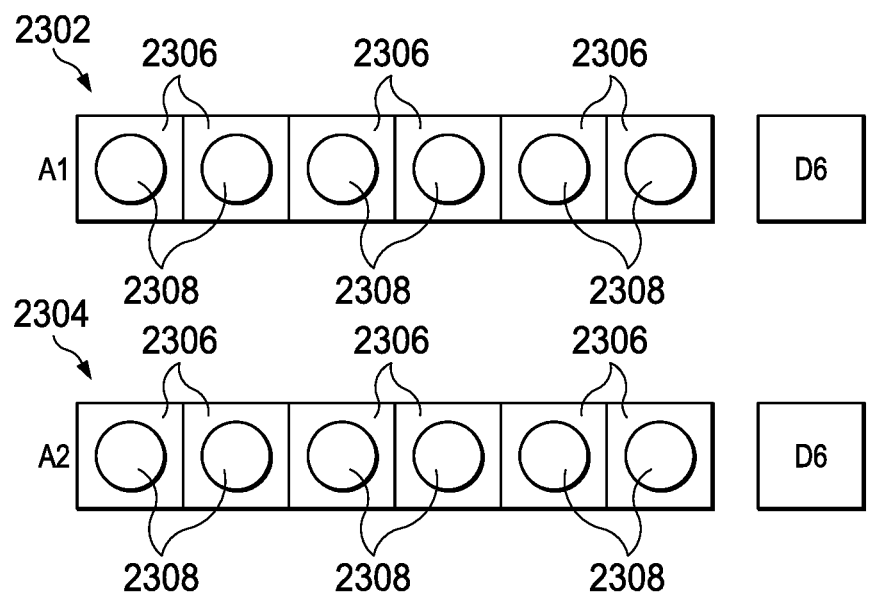
FIG. 23A illustrates a top view of one embodiment of antigen transdermal patch sheets.

Referring now to FIG. 23A, there is illustrated a top view of one embodiment of single dose antigen transdermal patch sheets 2302 and 2304. In this embodiment, single dose antigen transdermal patch sheets 2302 and 2304 each correspond to a different antigen, A1 and A2, respectively in order to deliver a cocktail of antigens at a prescribed dilutant level. Additionally, single dose antigen transdermal patch sheets 2302 and 2304 may each correspond to a particular dilutant level for that antigen, such as dilutant level D6. Each of the single dose antigen transdermal patch sheets 2302 and 2304 have a plurality of individual antigen specific single dose patches 2306, with each of the plurality of patches 2306 having an antigen carrier 2308 and each patch constituting a "single" dose of the associated antigen. The carrier 2308 may be a gel, such as a hydrogel, a cream, or another suitable carrier for an antigen. The carrier 2308 may have already included a single dose at a particular dilutant level of antigen, such as D6, or may only ship as the carrier with no antigen included, so that the antigen can later be added by someone such as a pharmacist. The carrier 2308 may also include a permeation enhancer. In the case of a hydrogel, the carrier may be produced using ingredients such as polyvinyl alcohol, sodium polyacrylate, acrylate polymers, and copolymers. Each of the plurality of patches 2306 may be cut from the sheet when a patch is needed. Antigen transdermal patch sheets 2302 and 2304 may thus be used for creating either single "single dose" antigen transdermal patches, or a single dose patch made up of the combination of antigens, such as both antigens A1 and A2, as will be described herein.

Figure 23B:
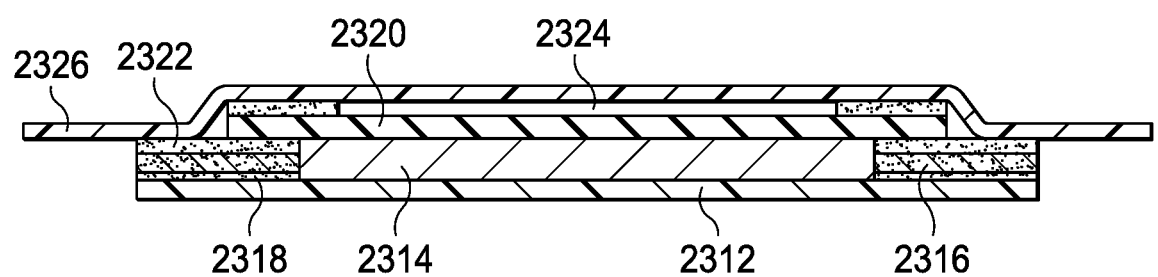
FIG. 23B illustrates a cross-sectional view of one embodiment of an antigen transdermal patch.

Referring now to FIG. 23B, there is illustrated a cross sectional view of one embodiment of a single dose antigen transdermal patch 2310. The single dose antigen transdermal patch 2310 may be one of the patches in the antigen transdermal patch sheets 2302 and 2304 described in FIG. 23A. The single dose antigen transdermal patch 2310 includes a back liner 2312. The back liner 2312 may be made of a material that is impervious to an antigen carrier 2314, and any antigen therein, used in the patch. The patch 2310 further includes a carrier platform 2316 upon which the antigen carrier 2314 is disposed. Upon creation of the patch, the antigen carrier 2314 may have a single dose of antigen at a prescribed dilutant level already contained within, or may later have an antigen added by someone such as a pharmacist for a single dose at a prescribed dilutant level. A first adhesive coating 2318 adheres the carrier platform 2316 to the back liner 2312. The carrier platform 2316 may be of a circular shape and may also have a recessed middle portion forming a cell that allows for the antigen carrier to be held within. The patch 2310 further includes a pharmaceutically diffusing cover 2320 that, when in use on a patient's skin, allows for the antigen to pass through into the patient's skin. The cover 2320 may be made of a tissue material, silicone, or some other porous material. The cover 2320 is held in place against the carrier platform 2316 by a second adhesive coating 2322. A third adhesive coating 2324 holds a peelable release liner 2326 over the cover 2320, to protect the contents of the patch. Once the patch is to be used, the peelable release liner 2326 is peeled away and the patch can then be applied to the skin, with the adhesive coating 2322 serving to adhere the patch to the skin. It is noted that the amount of antigen disposed in the patch will be a sufficient amount that, when released, will constitute a single dose "deliver" transdermally to the patent and, thus, more than an actual single dose of antigen will be disposed in the patch. The actual amount will vary depending upon the type of patch and the delivery mechanism.

Figure 24A:
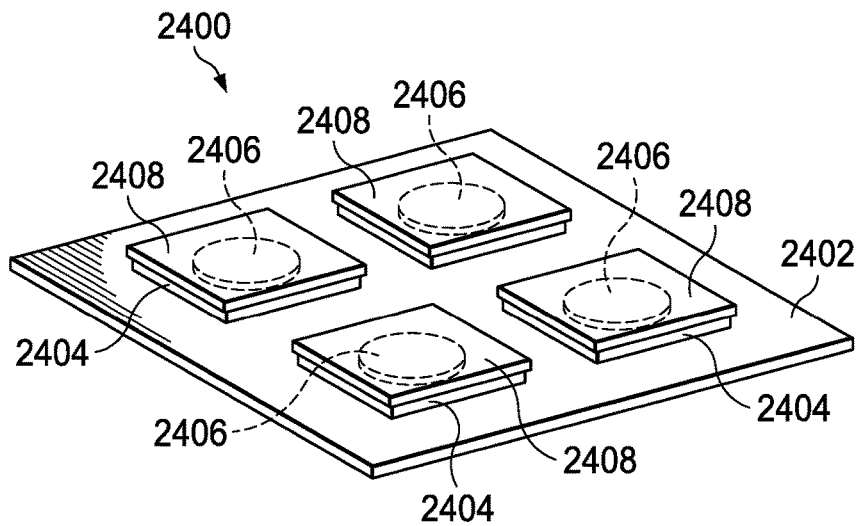
FIG. 24A illustrates a perspective view of one embodiment of a multi-antigen patch.
Figure 24B:
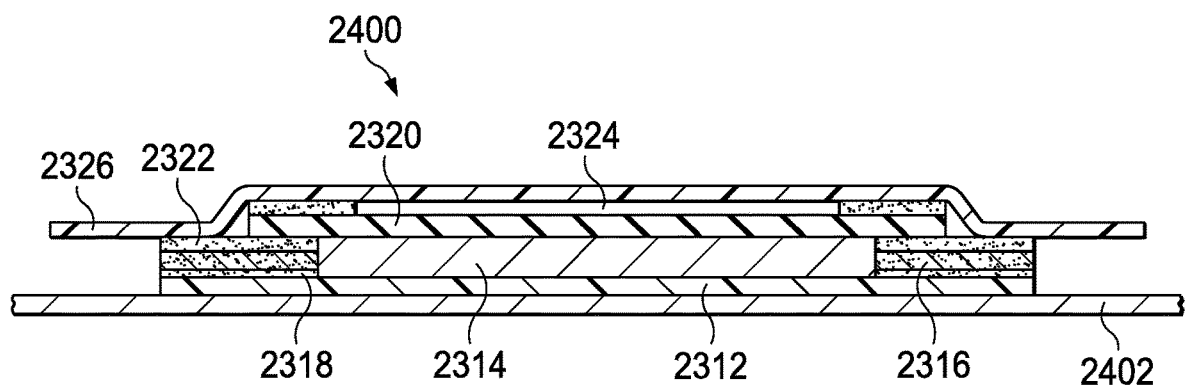
FIG. 24B illustrates a cross-sectional view of one embodiment of a multi-antigen patch.

Referring now to FIGS. 24A-B, there is illustrated one embodiment of a single dose multi-antigen patch 2400 at a particular dilutant level. The single dose multi-antigen patch 2400 includes a backing 2402 upon which multiple single dose antigen patches 2404 may reside, such as those described in FIGS. 23A and 23B, and each having an antigen carrier 2406, may be adhered to, in order to provide multiple single dose antigens in a single patch. The patches 2404 each also include a peelable release liner 2408. The backing 2402 may have designated spaces with adhesive coating for attaching each of the patches 2404, or the backs of the patches 2404 may have adhesive applied so they can be adhered to the backing 2402. In many embodiments, the patches 2404 are of a small enough scale that the single dose multi-antigen patch 2400 need not be bigger than a standard transdermal patch. The patch 2404 is identical to the patch described in FIG. 23B, except that they are attached to the backing 2402.

Figure 24C:
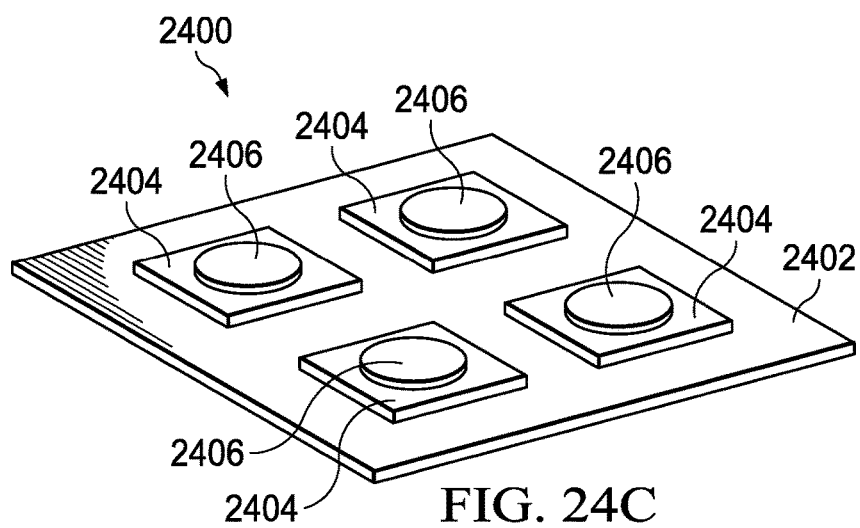
FIG. 24C illustrates a perspective view of one embodiment of a multi-antigen patch.
Figure 24D:
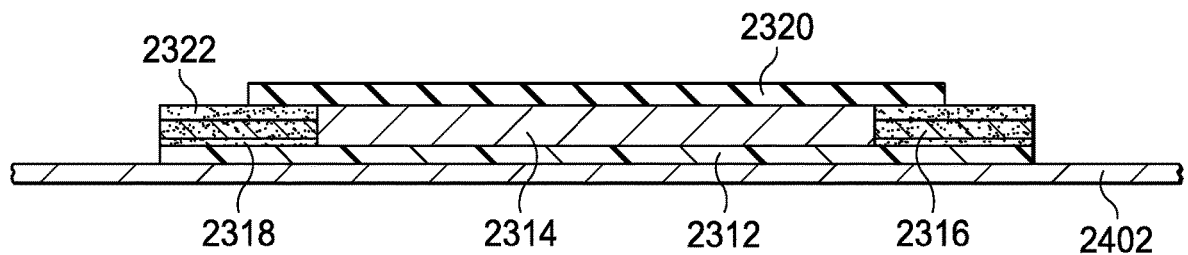
FIG. 24D illustrates a cross-sectional view of one embodiment of a multi-antigen patch.

Referring now to FIGS. 24C-D, there is illustrated the single dose multi-antigen (at a prescribed dilutant level) patch 2400 in the process of preparation. This will hereinafter be referred to as a "multi-antigen" patch, it being understood that each antigen is a single dose at a prescribed dilutant level. The multi-antigen patch 2400 now has had each of the peelable release liners 2408 removed from the patches 2404.

Figure 24E:
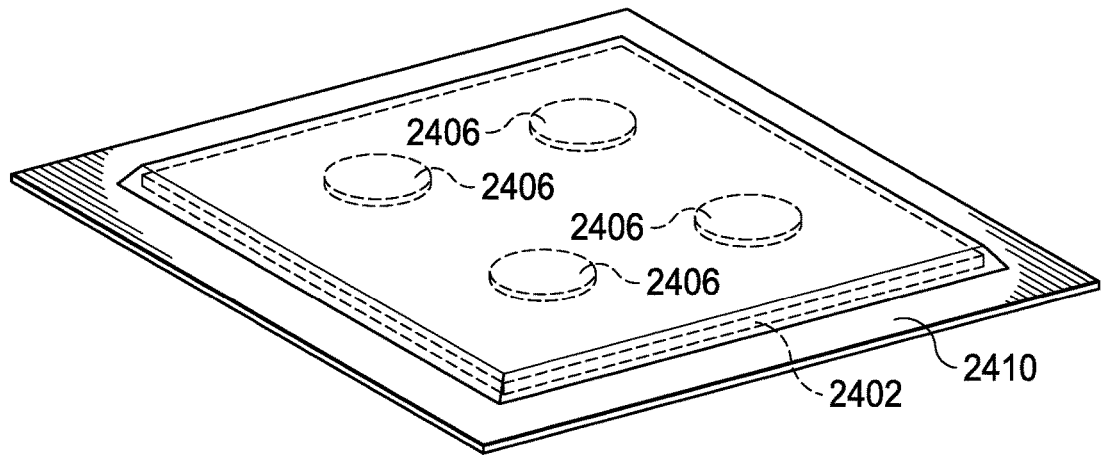
FIG. 24E illustrates a perspective view of one embodiment of a multi-antigen patch.
Figure 24F:
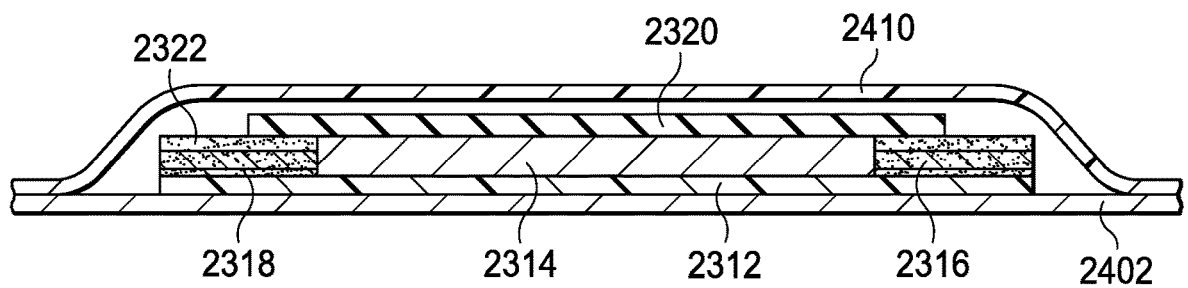
FIG. 24F illustrates a cross-sectional view of one embodiment of a multi-antigen patch.

Referring now to FIGS. 24E-F, there is illustrated the multi-antigen patch 2400 in the final stages of preparation. The multi-antigen patch 2400 has had a new peelable release liner 2410 that covers the entire multi-antigen patch 2400. The new peelable release liner 2410 may simply be applied after removing all of the liners 2408 of the patches 2404 if the antigen carriers 2406 already contain a single dose of the associated antigen. However, if the antigen carriers 2406 do not already contain antigen, then, before the new peelable release liner 2410 is applied, someone such as a pharmacist may remove the covers 2320 of the patches 2404 to add a single dose of antigen at a prescribed dilutant level to the antigen carriers 2406, replace the covers 2302, and then add the new peelable release liner 2410, noting that the terminology "add a single dose of antigen" is to be interpreted as adding a sufficient amount of the associated antigen to facilitate "delivery" of a single dose of antigen. A method of adding antigen to the antigen carriers is discussed hereinbelow.

Figure 25:
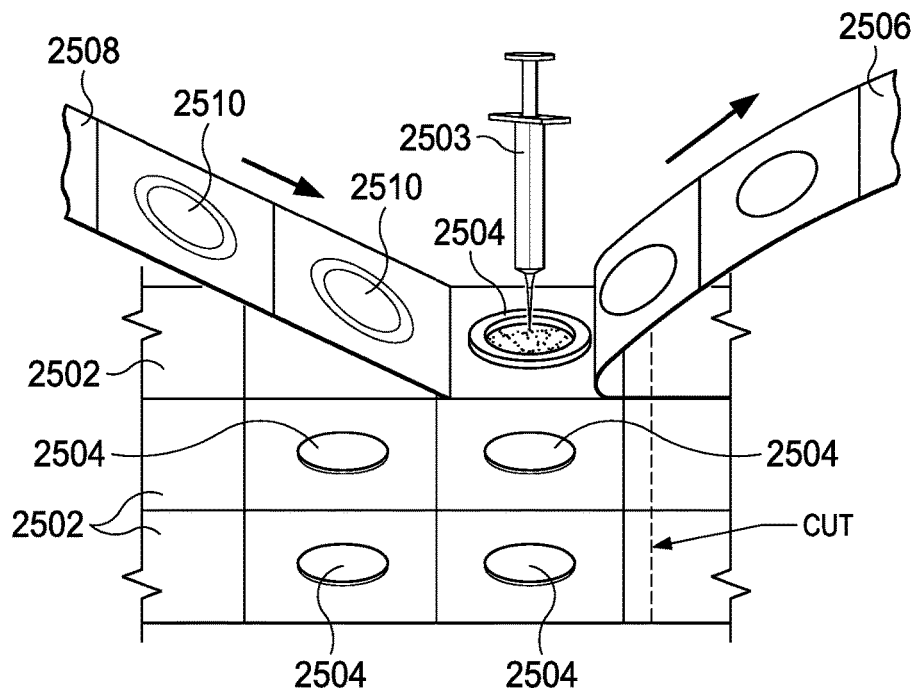
FIG. 25 illustrates one embodiment of a process for providing a single dose of antigen at a prescribed level in an antigen carrier.

Referring to FIG. 25, there is illustrated one embodiment of a process for providing a single dose of antigen at a prescribed level in an antigen carrier. There is provided a plurality of antigen patch sheets 2502, each having an antigen carrier cell 2504, the antigen carrier cell having a carrier such as a gel. The antigen patch sheets 2502 initially have disposed thereon a liner strip 2506. The liner strip 2506 is peeled away from the antigen patch sheets 2502, exposing the antigen carrier cell 2504. An antigen 2503 is then injected into the antigen carrier cell 2504. Once this is done, a peelable release liner 2508 is placed over the antigen patch sheets 2502, the peelable release liner 2508 also including a cover 2510 made of tissue, silicone, or some other porous material. The peelable release liner 2508 is applied in such a way that the cover 2510 covers the antigen carrier cell 2504. In this way, each of the antigen patch sheets 2502 may have a single dose of antigen at a prescribed dilutant level applied to each of the cells 2504 of that particular patch sheet. The antigen patch sheets 2502 may then be cut, in order to apply the antigen patches to a multi-antigen patch, such as that shown in FIGS. 24A-F.

Figure 26A:
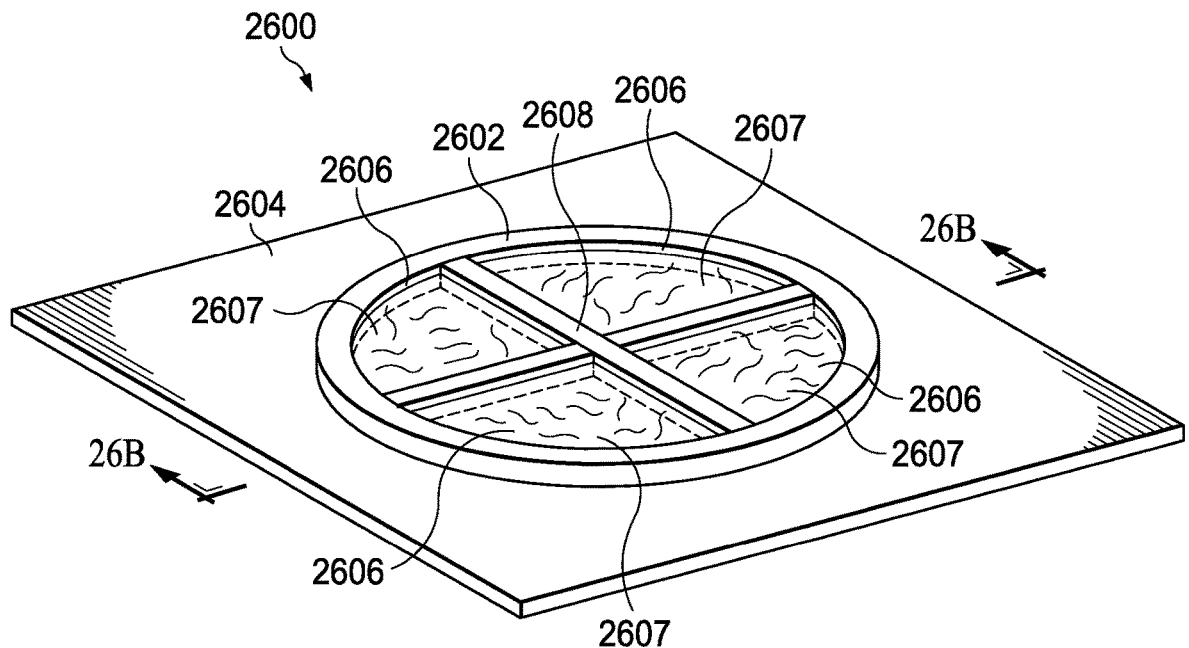
FIG. 26A illustrates a perspective view of one embodiment of a multi-antigen patch.

Referring now to FIG. 26A, there is illustrated one embodiment of a multi-antigen patch 2600. Multi-antigen patch 2600 includes a well 2602 disposed on a base 2604. The well 2602 is of a circular shape having recessed portions 2606 separated by raised cross portions 2608. The recessed portions 2606 contain a carrier gel 2607. While four recessed portions 2606 are illustrated in FIG. 26A, any number may be used.

Figure 26B:
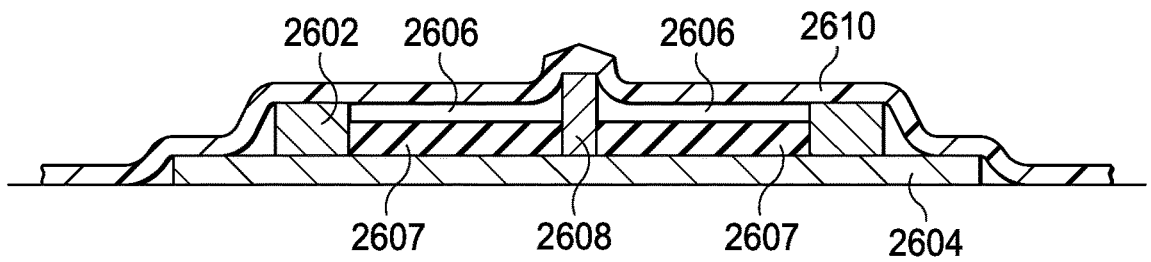
FIG. 26B illustrates a cross-sectional view of one embodiment of a multi-antigen patch.

Referring now to FIG. 26B, there is illustrated a cross-sectional view of the multi-antigen patch 2600. The multi-antigen patch 2600 has initially thereon a liner 2610 covering the base 2604 and the well 2602, in order to protect the carrier gel 2607 during activities such as shipping.

Figure 26C:
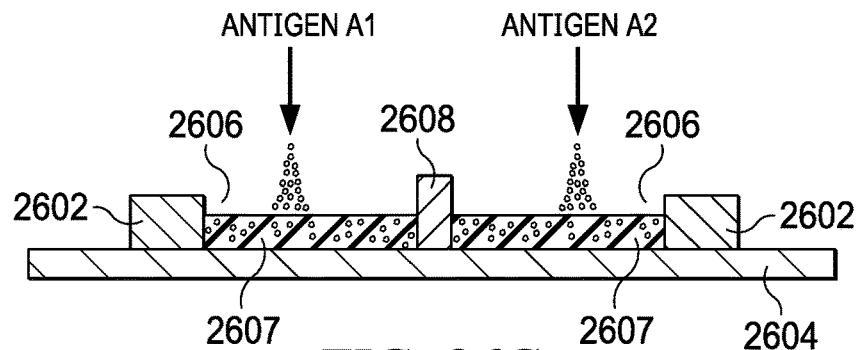
FIG. 26C illustrates a cross-sectional view of one embodiment of a multi-antigen patch after a liner is removed.

Referring now to FIG. 26C, there is illustrated another cross-sectional view of the multi-antigen patch 2600 after the liner 2610 is removed. Once the liner 2610 is removed, a single dose of antigen at a prescribed dilutant level, or multiple antigens at a prescribed dilutant level, may be inserted into the carrier gel 2607 of the recessed portions 2606 of the well 2602. This is shown in FIG. 26C where, with the liner 2610 removed, antigen A1 is inserted into the carrier gel 2607 of one of the recessed portions 2606 and antigen A2 is inserted into the carrier gel 2607 of another one of the recessed portions 2606. In this way, the carrier gel 2607 in each of the recessed portions 2606 of the well 2602 would then carry the desired amount of antigen.

Figure 26D:
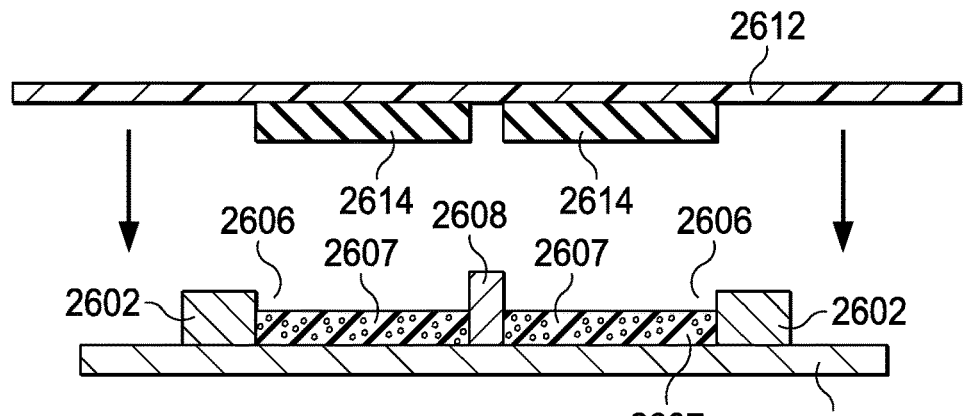
FIG. 26D and FIG. 26E illustrate a cross-sectional view of one embodiment of applying a peelable release liner to a multi-antigen patch.
Figure 26E:
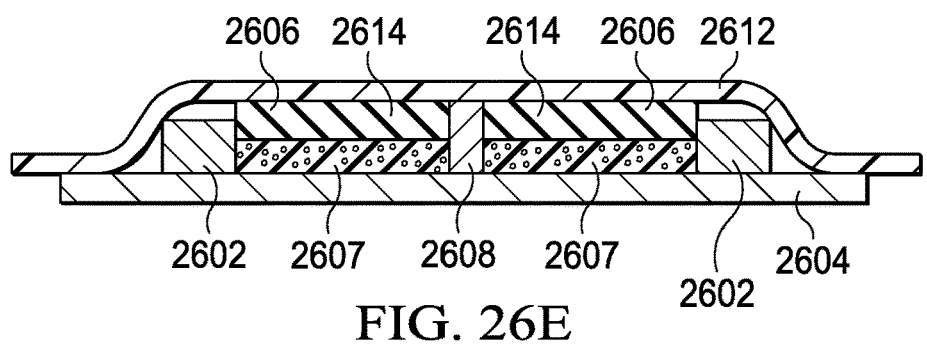

Referring now to FIG. 26D-E, there is illustrated a cross-sectional view of applying a peelable release liner 2612 to the multi-antigen patch 2600. The peelable release liner 2612 has spaced apart thereon covers 2614, one for each recessed portion 2606. When the peelable release liner 2612 is placed onto the multi-antigen patch 2600, each of the covers 2614 are inserted into or over a recessed portion 2606. The covers 2614 may be made of tissue, silicone, or some other material that allows for the antigen disposed within the gel 2607 to pass through the covers 2614 in order to come into contact with human skin. When the multi-antigen patch 2600 is to be used, the peelable release liner 2612 is removed and the covers 2614 are placed against the skin. It will be understood that, as described herein, the multi-antigen patch 2600 may be held in place on a patient's skin by an adhesive or some other means.

Figure 27:
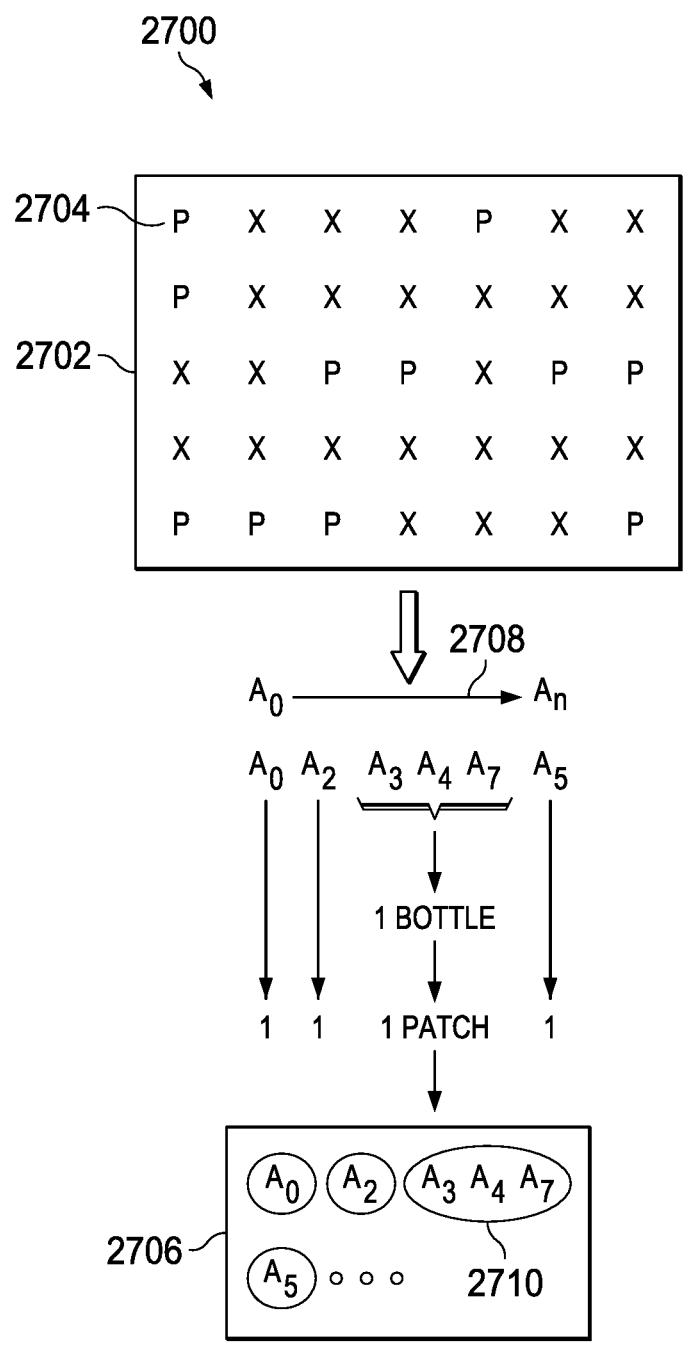
FIG. 27 illustrates one embodiment of a multi-antigen selection operation.

Referring now to FIG. 27, there is illustrated one embodiment of a multi-antigen patch antigen selection operation 2700. There is illustrated a custom patient-specific antigen results table 2702 resulting from the prick test. The table 2702 has a plurality of allergy indicators 2704, each having an allergy associated with each indicator having the letter "P" or "X," with "P" indicating a positive allergy result and "X" indicating a negative allergy result. This is used by the physician to create the script for the patient to create the patient-specific script. The results, when viewed by the medical practitioner, indicate the specific allergy reaction. For instance, the results may show that a patient is allergic to cat dander and certain types of pollen. Each of these would be marked with a "P" on the results table 2702, with an "X" marking the other allergies having a negative result. From the results table 2702, the proper antigens needed for the patient may be selected, the script generated, sent to the compounding pharmacist and applied to a multi-antigen patch 2706. If the patient is allergic to allergens $A_0$ through $A_n$, (reference number 2708), those allergens may be selected. Additionally, if certain antigens are commonly distributed as part of one antigen compound, such as a cocktail of pollen antigens, those may be applied to a single patch. This is similar to one bottle or dose of an antigen cocktail, as described herein, except provided in a patch. For example, and as illustrated in FIG. 27 (reference number 2708), if antigens $A_3$, $A_4$, and $A_7$, are typically be supplied together in the same antigen cocktail, then the multi-antigen patch 2706 may have antigens $A_3$, $A_4$, and $A_7$ within a single antigen carrier 2710.

Figure 28A:
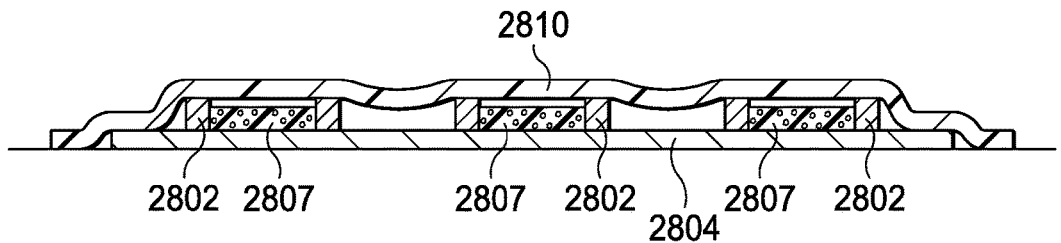
FIG. 28A illustrates a cross-sectional view of one embodiment of a multi-antigen patch.

Referring now to FIG. 28A, there is illustrated a cross-sectional view of one embodiment of a multi-antigen patch 2800. Multi-antigen patch 2800 includes wells 2802 disposed on a base 2804. The wells 2802 are of a circular shape having recessed portions containing a carrier gel 2807. Any number of wells may be present on a patch. The multi-antigen patch 2800 may initially have thereon a liner 2810 in order to protect the carrier gel 2807 during activities such as shipping.

Figure 28B:
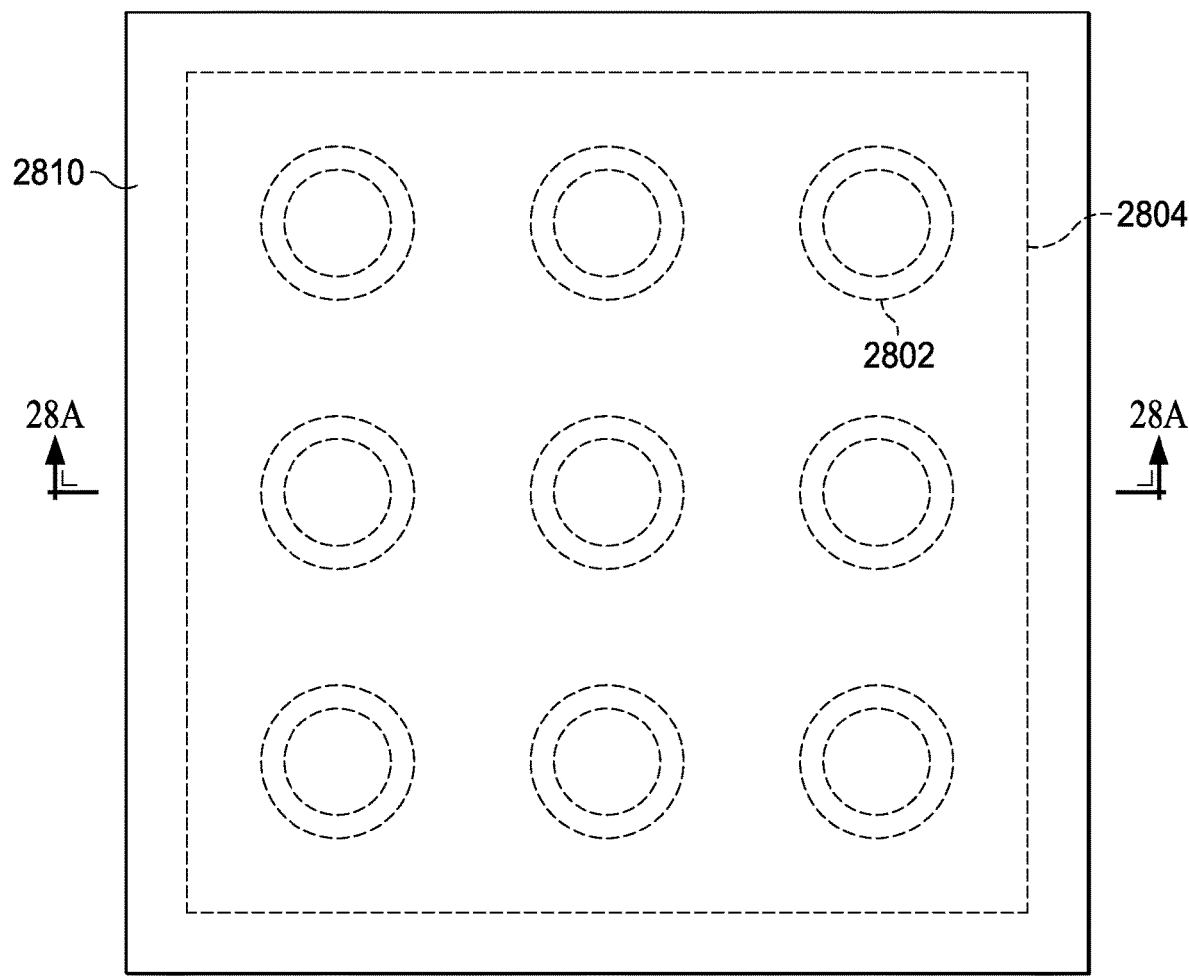
FIG. 28B illustrates a top view of one embodiment of a multi-antigen patch.

Referring now to FIG. 28B, there is illustrated a top view of the multi-antigen patch 2800. As stated, the multi-antigen patch 2800 has initially thereon a liner 2810 covering the base 2804 and the wells 2802, in order to protect the carrier gel 2807 during activities such as shipping.

Figure 28C:
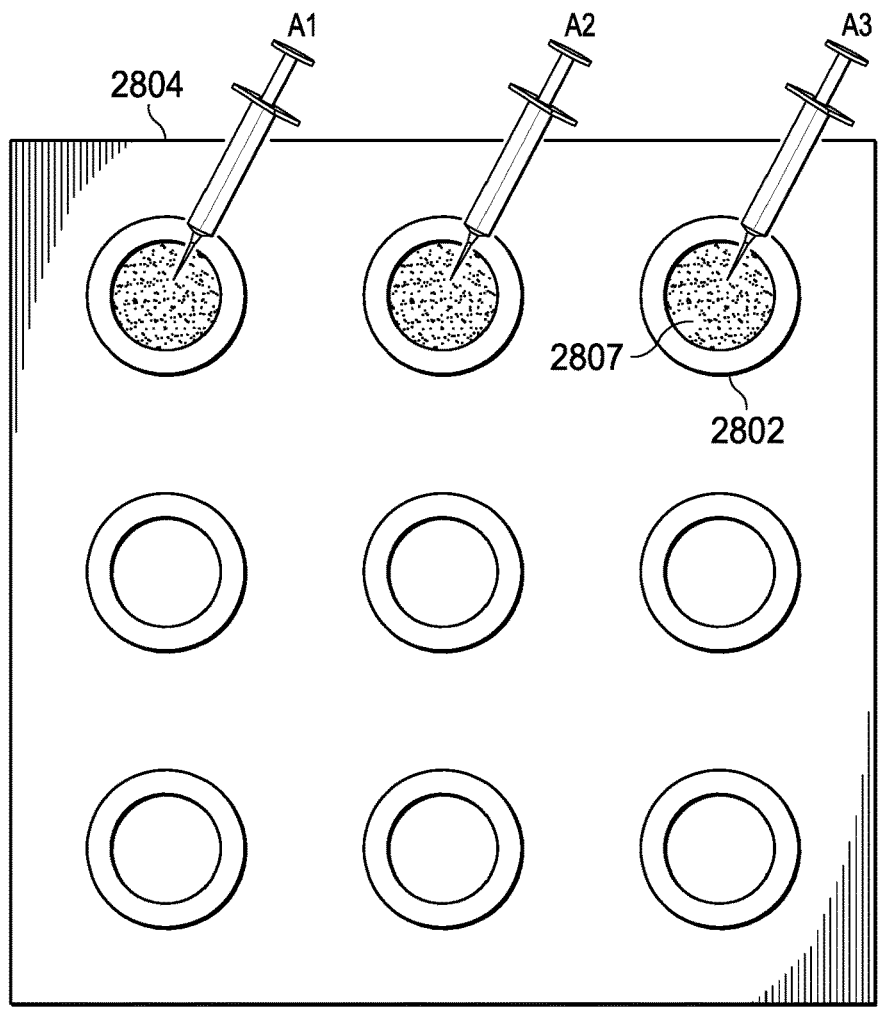
FIG. 28C illustrates a top view of one embodiment of a multi-antigen patch after a liner is removed.

Referring now to FIG. 28C, there is illustrated another top view of the multi-antigen patch 2800 after the liner 2810 is removed. Once the liner 2810 is removed, a single dose of antigen at a prescribed dilutant level, or multiple antigens at a prescribed dilutant level, may be inserted into the carrier gel 2807 in the wells 2802. This is shown in FIG. 28C where, with the liner 2810 removed, antigen A1 is inserted into the carrier gel 2807 of one of the recessed wells 2802, antigen A2 is inserted into the carrier gel 2807 of another one of the wells 2802, and antigen A3 is inserted into the carrier gel 2807 of another one of the wells 2802. This process may be repeated for each well 2602 disposed on the multi-antigen patch 2800. In this way, the carrier gel 2807 in each of wells 2802 would then carry the desired amount of antigen.

Figure 28D:
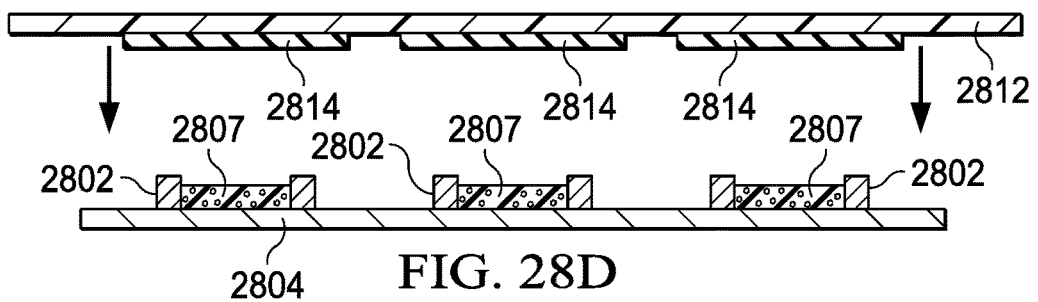
FIG. 28D and FIG. 28E illustrate a cross-sectional view of one embodiment of applying a peelable release liner to a multi-antigen patch.
Figure 28E:
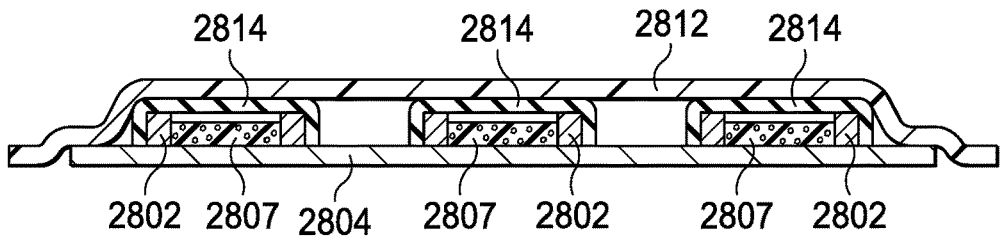

Referring now to FIG. 28D-E, there is illustrated a cross-sectional view of applying a peelable release liner 2812 to the multi-antigen patch 2800. The peelable release liner 2812 has spaced apart thereon covers 2814, one for each well 2802. When the peelable release liner 2812 is placed onto the multi-antigen patch 2800, each of the covers 2814 is inserted into or over an associated well 2802. The covers 2814 may be made of tissue, silicone, or some other material that allows for the antigen disposed within the gel 2807 to pass through the covers 2814 in order to come into contact with human skin. When the multi-antigen patch 2800 is to be used, the peelable release liner 2812 is removed and the covers 2814 are placed against the skin. It will be understood that, as described herein, the multi-antigen patch 2800 may be held in place on a patient's skin by an adhesive or some other means. This thus allows for a single dose of each antigen that is included on the patch to be transdermally delivered. Further, once the patch is created, then the pharmacist need only provide the script and the antigen base concentrate NDCs utilized, the dilution procedure and the carrier to the PBM database in order to determine the available benefits, as described in detail hereinabove.

It will be understood by one skilled in the art that variations made be made to the patch without deviating from the present inventive concept. For instance, the patch may be a single-layer drug-in-adhesive, having the drug within the adhesive layer, a multi-layer drug-in-adhesive, a matrix system patch, or rate controlled membrane patch.

Although the preferred embodiment has been described in detail, it should be understood that various changes, substitutions and alterations can be made therein without departing from the spirit and scope of the invention as defined by the appended claims.

What is claimed is:

1. A multi-antigen patch, comprising:
    a backing;
    a carrier platform including a first adhesive coating which adheres the carrier platform to the backing, wherein a plurality of carrier platforms is adhered to the backing;
    a plurality of wells disposed in the carrier platform, wherein the plurality of wells includes a rim portion protruding above a surface of the carrier platform and an interior portion lower than the rim portion;
    a carrier in the interior portion of each of the plurality of wells, each of the plurality of wells containing one or more antigens;
    a second adhesive coating formed on the surface of the backing outside a perimeter of the plurality of wells, wherein the second adhesive coating adheres to a skin of a patient;
    a first liner disposed over the backing and the plurality of wells, wherein, after removal of the first liner, the one or more antigens are inserted into the carrier of each of the plurality of wells; and a second release liner associated with the multi-antigen patch, wherein the second release liner is installed over the backing and the plurality of wells after removal of the first liner, wherein, during application of the second release liner to the multi-antigen patch, a plurality of covers coupled to the second release liner are inserted into the plurality of wells, wherein, when the second release liner is removed from the multi-antigen patch, the plurality of covers remain inserted into the plurality of wells, wherein each of the plurality of covers protrude above the rim portion of the plurality of wells, and wherein the plurality of covers are of a material that allows for antigens to pass through the plurality of covers.

2. The multi-antigen patch of claim 1, wherein the material includes one of tissue paper or silicone.

3. The multi-antigen patch of claim 1, wherein the plurality of wells includes four wells divided into quadrants, wherein the quadrants are defined by the rim portion.

4. The multi-antigen patch of claim 3, wherein each of the four wells includes a different antigen within the carrier.

5. The multi-antigen patch of claim 1, wherein each of the plurality of wells includes a single dose of the one or more antigens at a prescribed diluted level.

* * * * *